US009446150B2

(12) United States Patent
Lanza et al.

(10) Patent No.: US 9,446,150 B2
(45) Date of Patent: Sep. 20, 2016

(54) PARTICLES FOR IMAGING

(75) Inventors: Gregory M. Lanza, St. Louis, MO (US); Samuel A. Wickline, St. Louis, MO (US); Dipanjan Pan, St. Louis, MO (US); Angana Senpan, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 352 days.

(21) Appl. No.: 12/682,094

(22) PCT Filed: Oct. 9, 2008

(86) PCT No.: PCT/US2008/079404
§ 371 (c)(1),
(2), (4) Date: Aug. 12, 2010

(87) PCT Pub. No.: WO2009/049083
PCT Pub. Date: Apr. 16, 2009

(65) Prior Publication Data
US 2010/0297019 A1   Nov. 25, 2010

Related U.S. Application Data

(60) Provisional application No. 60/978,678, filed on Oct. 9, 2007, provisional application No. 60/981,192, filed on Oct. 19, 2007.

(51) Int. Cl.
A61K 49/00 (2006.01)
A61K 49/04 (2006.01)
A61K 49/08 (2006.01)
A61K 49/10 (2006.01)
A61K 49/14 (2006.01)
A61K 49/18 (2006.01)
B82Y 5/00 (2011.01)

(52) U.S. Cl.
CPC ....... *A61K 49/0002* (2013.01); *A61K 49/0065* (2013.01); *A61K 49/0082* (2013.01); *A61K 49/0428* (2013.01); *A61K 49/085* (2013.01); *A61K 49/103* (2013.01); *A61K 49/14* (2013.01); *A61K 49/1809* (2013.01); *A61K 49/1839* (2013.01); *B82Y 5/00* (2013.01)

(58) Field of Classification Search
CPC ............ A61K 49/0002; A61K 49/0065; A61K 49/0082; A61K 49/0428; A61K 49/103; A61K 49/14; A61K 49/1809; A61K 49/1839; A61K 49/085; B82Y 5/00
USPC .......... 424/490, 9.4, 9.42, 9.45, 9.3, 9.32, 424/9.321, 9.323, 9.5, 9.51
See application file for complete search history.

(56) References Cited

U.S. PATENT DOCUMENTS

| | | | |
|---|---|---|---|
| 3,215,572 A | 11/1965 | Papell | |
| 4,297,623 A | 10/1981 | Dupont | |
| 5,077,036 A | 12/1991 | Long, Jr. | |
| 5,114,703 A | 5/1992 | Wolf et al. | |
| 5,171,755 A | 12/1992 | Kaufman et al. | |
| 5,213,788 A * | 5/1993 | Ranney ............. | A61K 47/4823 424/617 |
| 5,260,306 A | 11/1993 | Boardman et al. | |
| 5,304,325 A | 4/1994 | Kaufman et al. | |
| 5,350,571 A | 9/1994 | Kaufman et al. | |
| 5,393,524 A | 2/1995 | Quay | |
| 5,403,575 A | 4/1995 | Kaufman et al. | |
| 5,534,499 A | 7/1996 | Ansell | |
| 5,690,907 A | 11/1997 | Lanza et al. | |
| 5,780,010 A | 7/1998 | Lanza et al. | |
| 5,820,848 A | 10/1998 | Boni et al. | |
| 5,958,371 A | 9/1999 | Lanza et al. | |
| 5,989,520 A | 11/1999 | Lanza et al. | |
| 6,368,586 B1 | 4/2002 | Jacob | |
| 6,413,544 B1 | 7/2002 | Smyth-Templeton et al. | |
| 6,491,903 B1 | 12/2002 | Forster et al. | |
| 6,579,846 B1 | 6/2003 | Zirnstein et al. | |
| 7,022,313 B2 | 4/2006 | O'Connor et al. | |
| 2002/0034536 A1 | 3/2002 | Perkins et al. | |
| 2003/0157179 A1* | 8/2003 | Blum et al. ............ | 424/489 |
| 2003/0185879 A1 | 10/2003 | Boulikas | |
| 2004/0142474 A1 | 7/2004 | Mahato et al. | |
| 2004/0229945 A1 | 11/2004 | Satchi-Fainaro et al. | |
| 2005/0037050 A1 | 2/2005 | Weber | |
| 2005/0065026 A1* | 3/2005 | Okubo ............ | B01J 23/63 502/339 |
| 2005/0079131 A1* | 4/2005 | Lanza et al. ............. | 424/1.11 |
| 2005/0095267 A1 | 5/2005 | Campbell et al. | |
| 2006/0008461 A1 | 1/2006 | Yatvin et al. | |
| 2006/0015261 A1 | 1/2006 | Mann et al. | |
| 2006/0159619 A1 | 7/2006 | Becker et al. | |
| 2006/0228299 A1 | 10/2006 | Thorpe et al. | |

(Continued)

FOREIGN PATENT DOCUMENTS

EP   2209420        7/2010
WO   96/20698 A2   7/1996

(Continued)

OTHER PUBLICATIONS

Mandal et al., Langmuir, 2005, 21, p. 4175-4179.*

(Continued)

*Primary Examiner* — Michael G Hartley
*Assistant Examiner* — Leah Schlientz
(74) *Attorney, Agent, or Firm* — Polsinelli PC

(57) ABSTRACT

The invention encompasses particles comprising metal atoms, methods of making the particles, and methods for using the particles. In particular, the particles may be used to image biological tissues or to deliver a bioactive agent.

21 Claims, 14 Drawing Sheets

(56) References Cited

U.S. PATENT DOCUMENTS

| | | | |
|---|---|---|---|
| 2006/0264397 | A1 | 11/2006 | Kucera et al. |
| 2007/0020308 | A1 | 1/2007 | Richard et al. |
| 2007/0110777 | A1 | 5/2007 | Joabsson et al. |
| 2007/0154539 | A1 | 7/2007 | Fountain |
| 2008/0269875 | A1 | 10/2008 | Zhao |
| 2008/0286321 | A1 | 11/2008 | Reneker et al. |
| 2008/0286372 | A1 | 11/2008 | Pacetti et al. |
| 2009/0148383 | A1 | 6/2009 | Peter |
| 2009/0163437 | A1 | 6/2009 | Rusconi |
| 2009/0202429 | A1 | 8/2009 | Diacovo et al. |
| 2009/0208548 | A1* | 8/2009 | Mason et al. ............ 424/405 |
| 2010/0028994 | A1 | 2/2010 | DeSimone et al. |
| 2010/0297007 | A1 | 11/2010 | Lanza et al. |
| 2011/0123438 | A1 | 5/2011 | Wickline |
| 2013/0064765 | A1 | 3/2013 | Myerson et al. |
| 2013/0122100 | A1 | 5/2013 | Lanza et al. |

FOREIGN PATENT DOCUMENTS

| | | |
|---|---|---|
| WO | 01/74337 A1 | 10/2001 |
| WO | 03/015831 A1 | 2/2003 |
| WO | 2004/017907 A2 | 3/2004 |
| WO | 2005/014051 A1 | 2/2005 |
| WO | 2006072943 A1 | 7/2006 |
| WO | 2006072943 A2 | 7/2006 |
| WO | 2006117720 A2 | 11/2006 |
| WO | 2007034359 A2 | 3/2007 |
| WO | 2007/106683 A2 | 9/2007 |
| WO | 2008/063157 A2 | 5/2008 |
| WO | 2008/109712 A2 | 9/2008 |
| WO | 2009/049083 A1 | 4/2009 |
| WO | 2009/049089 A1 | 4/2009 |
| WO | 2011/084700 A1 | 7/2011 |
| WO | 2011/130674 A1 | 10/2011 |
| WO | 2011/133635 A2 | 10/2011 |
| WO | 2014/179793 A1 | 11/2014 |

OTHER PUBLICATIONS

Cho et al., J. Agric. Food Chem., 2002, 50, p. 5704-510.*
Oyewumi et al., Drug Development and Industrial Pharmacy, 2002, 28(3), p. 317-328.*
International Search Report and Written Opinion dated Dec. 24, 2008 from related International application No. PCT/US08/079404, 8 pgs.
Benson, Present status of coronary artery disease, Arch Pathol Lab Med, 1926; vol. 2:876-916.
Constantinides, Plaque fissures in human coronary thrombosis, J Atheroscler Res, 1966; vol. 6:1-17.
Brown, Incomplete lysis of thrombus in the moderate underlying atherosclerotic lesion during intracoronary infusion of streptokinase for acute myocardial infarction: quantitative angiographic observations, Circulation, 1986; vol. 73:653-661.
Ambrose, Angiographic progression of coronary artery disease and the development of myocardial infarction, J. Am. Coll Cardiol, 1988; vol. 12:56-62.
Glagov, Compensatory enlargement of human atherosclerotic coronary arteries, N Engl J Med, 1987; vol. 316:1371-1375.
De Korte, Characterization of plaque components and vulnerability with intravascular ultrasound elastography, Phys Med Biol, 2000; vol. 45:1465-1475.
Cerqueira, Current status of radionuclide tracer imaging of thrombi and atheroma. Semin Nucl Med 1999; vol. 29:339-351.
Casscells, Thermal detection of cellular infiltrates in living atherosclerotic plaques: possible implications for plaque rupture and thrombosis, Lancet, 1996; vol. 347:1447-1451.
Moody, Direct magnetic resonance imaging of carotid artery thrombus in acute stroke, Lancet, 1999; vol. 353:122-123.
Hofman, Quantification of inplane motion of the coronary arteries during the cardiac cycle: Implications for acquisition window duration for MR flow quantification, Journal of Magnetic Resonance Imaging, 1998; vol. 8(3):568576.

Gilchrist, Selective inductive heating of lymph nodes, Ann Surg, 1957; vol. 146(4):596-606.
Thorek, Superparamagnetic Iron Oxide Nanoparticle Probes for Molecular Imaging, Annals of Biomedical Engineering, Jan. 2006; vol. 34(1):23-38.
Landsfester, Encapsulated magnetite particles for biomedical application, J. Phys: Condens Matter, 2003; vol. 15:S1345-S1361.
Moralesa, Contrast nanoparticles for MRI based on iron oxide nanoparticles prepared by laser pyrolysis, Journal of Magnetism and Magnetic Materials, 2003; vol. 266:102-109.
Yang, Preparation of poly-caprolactone nanoparticles containing magnetite for magnetic drug carrier, International Journal of Pharmaceutics, Nov. 6, 2006; vol. 324(2):185-190.
Xu, Encapsulation of nanosized magnetic iron oxide by polyacrylamide via inverse miniemulsion polymerization, Journal of Magnetism and Magnetic Materials, Jun. 2004; vol. 277(1-2):136-143.
Montagnea, Preparation and characterization of narrow sized (o/w) magnetic emulsion, Journal of Magnetism and Magnetic Materials, Sep. 2002; vol. 250:302-312.
Liu, Preparation and characterization of biodegradable magnetic carriers by single emulsion-solvent evaporation, Journal of Magnetism and Magnetic Materials, Apr. 2007; vol. 311(1):84-87.
Deng, Magnetic and conducting Fe3O4—cross-linked polyaniline nanoparticles with core-shell structure, Polymer, Apr. 2002; vol. 43(8):2179-2184.
Liu, Surface Modification and Characterization of Magnetic Polymer Nanospheres Prepared by Miniemulsion Polymerization, Langmuir, 2004; vol. 20:10278-0282.
Deng, Preparation of magnetic polymeric particles via inverse microemulsion polymerization process, Journal of Magnetism and Magnetic Materials, Feb. 2003; vol. 257(1):69-78.
Bibette, Monodisperse ferrofluid emulsions, J. Magn. Magn. Mater., 1992; vol. 122:37-41.
Rosenweig, Magnetic Fluids, Int. Sci. Technol., Jul. 1966, pp. 48-56.
Raj, Commercial applications of ferrofluids, J. Magn. Magn. Mater., 1990; vol. 85:233-245.
Charles, Some applications of magnetic fluids—use as an ink and in microwave systems, J. Magn. Magn. Mater., 1987; vol. 65:350-358.
Roath, Biological and biomedical aspects of magnetic fluid technology, J. Magn. Magn. Mater., 1993; vol. 122:329-334.
Roger, Some biomedical applications of ferrofluids, Eur. Phys. J., 1999; vol. 5:321-325.
Davies, The effect of temperature and oleate adsorption on the growth of maghemite particles, J. Magn. Magn. Mater., 1993; vol. 122:24-28.
Feltin, New technique for synthesizing iron ferrite magnetic nanosized particles, Langmuir, 1997; vol. 13:3927-3933.
Dresco, Preparation and Properties of Magnetite and polymer magnetite nanoparticles, Langmuir, 1999; vol. 15:1945-1951.
International Search Report and Written Opinion dated Dec. 24, 2008 from related International Application No. PCT/US08/79404, 8 pgs.
First Office action dated Jul. 20, 2011 from related CN Appln. No. 200880117661.5, 11 pgs.
Second Office action dated Jun. 4, 2012 from related CN Appln. No. 200880117661.5, 17 pgs.
Third Office action dated Jan. 7, 2013 from related CN Appln. No. 200880117661.5, 13 pgs.
Office action dated Feb. 25, 2013 from related U.S. Appl. No. 12/910,385, 20 pgs.
Acharyya et al., "Interplay of IKK/NF-κB signaling in macrophages and myofibers promotes muscle degeneration in Duchenne muscular dystrophy", The Journal of Clinical Investigation, 2007, pp. 889-901, vol. 117, No. 4.
Andersson et al., "Heparin cofactor II activity in plasma: Application of an automated assay method to the study of a normal adult population", Scandinavian Journal of Haematology, 1986, pp. 96-102, vol. 36.
Angelova et al., "Liposome Electroformation", Faraday Discuss. Chem. Soc., 1986, pp. 303-311, vol. 81.

(56) References Cited

OTHER PUBLICATIONS

Ansell et al., "The Pharmacology and Management of the Vitamin K Antagonists", CHEST, 2004, pp. 204S-233S, vol. 126, No. 3.
Bacia et al., "Fluorescence Correlation Spectroscopy", Methods in Molecular Biology, 2007, pp. 73-84, vol. 398.
Baud et al., "Is NF-κB a good target for cancer therapy? Hopes and pitfalls", Nat Rev Drug Discov., 2009, pp. 33-40, vol. 8, No. 1.
Bernal-Mizrachi et al., "The role of NF-κB-1 and NF-κB-2-mediated resistance to apoptosis in lymphomas", PNAS, 2006, pp. 9220-9225, vol. 103, No. 24.
Bertina et al., "Hereditary Heparin Cofactor II Deficiency and the Risk of Development of Thrombosis", Journal of Thrombosis and Haemostasis, 1987, pp. 196-200, vol. 57, No. 2.
Bhoj et al., "Ubiquitylation in innate and adaptive immunity", Nature, 2009, pp. 430-437, vol. 458.
Bidwell III et al., "Therapeutic peptides for cancer therapy. Part I—peptide inhibitors of signal transduction cascades", Expert Opin. Drug Deliv., 2009, pp. 1033-1047, vol. 6, No. 10.
Bode et al., "The refined 1.9 Å crystal structure of human α-thrombin: interaction with D-Phe-Pro-Arg chloromethylketone and significance of the Tyr-Pro-Pro-Trp insertion segment", The EMBO Journal, 1989, pp. 3467-3475, vol. 8, No. 11.
Bode et al., "The refined 1.9-Å X-ray crystal structure of D-Phe-Pro-Arg chloromethylketone-inhibited human α-thrombin: Structure analysis, overall structure, electrostatic properties, detailed active-site geometry, and structure-function relationships", Protein Science, 1992, pp. 426-471, vol. 1.
Bousser, "Antithrombotic Agents in the Prevention of Ischemic Stroke", Cerebrovascular Diseases, 2009, pp. 12-19, vol. 27 (suppl 3).
Bowen, "Particle Size Distribution Measurement from Millimeters to Nanometers and from Rods to Platelets", Journal of Dispersion Science and Technology, 2002, pp. 631-662, vol. 23, No. 5.
Boxus et al., "The HTLV-I Tax interactome", Retrovirology, 2008, pp. 76-99, vol. 5.
Bretschneider et al., "Evidence for functionally active protease-activated receptor-4 (PAR-4) in human vascular smooth muscle cells", British Journal of Pharmacology, 2001, pp. 1441-1446, vol. 132, No. 7.
Bretschneider et al., "Evidence for functionally active protease-activated receptor-3 (PAR-3) in human vascular smooth muscle cells", Journal of Thrombosis and Haemostasis, 2003, pp. 704-709, vol. 90.
Brownlie et al., "PEI-based vesicle-polymer hybrid gene delivery system with improved biocompatibility", International Journal of Pharmaceutics, 2004, pp. 41-52, vol. 274.
Caruthers et al., "Anti-angiogenic perfluorocarbon nanoparticles for diagnosis and treatment of atherosclerosis", WIREs Nanomedicine and Nanobiotechnology, 2009, pp. 311-323, vol. 1.
Collen et al., "In vivo studies of a synthetic inhibitor of thrombin", J. Lab. Clin. Med., 1982, pp. 76-83, vol. 99, No. 1.
Coughlin, "Thrombin signalling and protease-activated receptors", Nature, 2000, pp. 258-264, vol. 407.
Davies, "Anatomic Features in Victims of Sudden Coronary Death, Coronary Artery Pathology", Circulation, Supplement I, 1992, pp. I19-I24, vol. 85, No. 1.
Di Cera, "Thrombin", Mol Aspects Med., 2008, pp. 203-254, vol. 29, No. 4.
Dubertret et al., "In Vivo Imaging of Quantum Dots Encapsulated in Phospholipid Micelles", Science, 2002, pp. 1759-1762, vol. 298.
Duguid, "Thrombosis As a Factor in the Pathogenesis of Coronary Atherosclerosis", J Path Bact., 1946, pp. 207-212, vol. 58.
Duguid, "Thrombosis As a Factor in the Pathogenesis of Aortic Atherosclerosis", J Path Bact., 1948, pp. 57-61, vol. 60.
Extended European Search report from related European Patent Application No. EP 10 84 2655, dated May 27, 2015; 12 pgs.
Extended European Search report from related European Patent Application No. EP 11769698.9, dated May 6, 2014; 8 pgs.
Extended European Search Report from related European Patent Application No. EP 08 83 7973, dated Jan. 2, 2014; 9 pgs.

Fareed et al., "Changing trends in anti-coagulant therapies. Are heparins and oral anti-coagulants challenged?", International Journal of Angiology, 2008, pp. 176-192, vol. 27, No. 3.
Flacke et al., "Novel MRI Contrast Agent for Molecular Imaging of Fibrin: Implications for Detecting Vulnerable Plaques", Circulation, 2001, pp. 1280-1285, vol. 104.
Flaim, "Pharmacokinetics and Side Effects of Perfluorocarbon-Based Blood Substitutes", Artificial Cells, Blood Substitutes, and Immobilization Biotechnology, 1994, pp. 1043-1054, vol. 22, No. 4.
Forrest et al., "Partial Acetylation of Polyethylenimine Enhances In Vitro Gene Delivery", Pharmaceutical Research, 2004, pp. 365-371, vol. 21, No. 2.
Furie et al., "Mehanisms of Thrombus Formation", The New England Journal of Medicine, 2008, pp. 938-949, vol. 359, No. 9.
Garg et al., "Nuclear transcription factor-κB as a target for cancer drug development", Leukemia, 2002, pp. 1053-1068, vol. 16.
Ghigliotti et al., "Prolonged Activation of Prothrombin on the Vascular Wall After Arterial Injury", Arteriosclerosis, Thrombosis, and Vascular Biology, 1998, pp. 250-257, vol. 18.
Gross et al., "New Antithrombotic Drugs", Clinical Pharmacology & Therapeutics, 2009, pp. 139-146, vol. 86, No. 2.
Grossman et al., "Development of leukemia in mice transgenic for the tax gene of human T-cell leukemia virus type I", Proc. Natl. Acad. Sci. USA, 1995, pp. 1057-1061, vol. 92.
Grossman et al., "Cytokine Expression and Tumorigenicity of Large Granular Lymphocytic Leukemia Cells From Mice Transgenic for the tax Gene of Human T-Cell Leukemia Virus Type I", Blood, 1997, pp. 783-794, vol. 90, No. 2.
Hess et al., "Biological and Chemical Applications of Fluorescence Correlation Spectroscopy: A Review", Biochemistry, 2002, pp. 697-705, vol. 41, No. 3.
Hirano, "The Roles of Proteinase-Activated Receptors in the Vascular Physiology and Pathophysiology", Arteriosclerosis, Thrombosis, and Vascular Biology, 2007, pp. 27-36, vol. 27.
Hirsh et al., "Beyond Unfractionated Heparin and Warfarin: Current and Future Advances", Circulation, 2007, pp. 552-560, vol. 116.
Hu et al., "Imaging of Vx-2 rabbit tumors with αvβ3-integrin-targeted 111In nanoparticles", International Journal of cancer, 2007, pp. 1951-1957, vol. 120.
Qiu et al., "Novel, Fluorescent, Magnetic, Polysaccharide-Based Microsphere for Orientation, Tracing, and Anticoagulation: Preparation and Characterization", Biomacromolecules, 2005, pp. 1041-1047, vol. 6, No. 2.
Rhoades et al., "Quantification of α-Synuclein Binding to Lipid Vesicles Using Fluorescence Correlation Spectroscopy", Biophysical Journal, 2006, pp. 4692-4700, vol. 90, No. 12.
Rothwarf et al., "IKK-γ is an essential regulatory subunit of the IκB kinase complex", Nature, 1998, pp. 297-300, vol. 395.
Schwartz et al., "Microemboli and Microvascular Obstruction in Acute Coronary Thrombosis and Sudden Coronary Death", Journal of the American College of Cardiology, 2009, pp. 2167-2173, vol. 54, No. 23.
Sie et al., "Constitutional Heparin Co-Factor II Deficiency Associated with Recurrent Thrombosis", The LANCET, 1985, pp. 414-416, vol. 2.
Smale, "Selective Transcription in Response to an Inflammatory Stimulus", Cell, 2010, pp. 833-844, vol. 140, No. 6.
Soman et al., "Synthesis and Characterization of Stable Fluorocarbon Nanostructures as Drug Delivery Vehicles for Cytolytic Peptides", Nano Lett., 2008, pp. 1131-1136, vol. 8, No. 4.
Soman et al., "Molecularly targeted nanocarriers deliver the cytolytic peptide melittin specifically to tumor cells in mice, reducing tumor growth", The Journal of Clinical Investigation, 2009, pp. 2830-2842, vol. 119, No. 9.
Srivastava et al., "Progress in the Design of Low Molecular Weight Thrombin Inhibitors", Medicinal Research Reviews, 2005, pp. 66-92, vol. 25, No. 1.
Su, "Assembly of polydiacetylene vesicles on solid substrates", Journal of Colloid and Interface Science, 2005, pp. 271-276, vol. 292.
Sun et al., "Persistent activation of NF-κB by the Tax transforming protein of HTLV-1: hijacking cellular IκB kinases", Oncogene, 1999, pp. 6948-6958, vol. 18.

(56) References Cited

OTHER PUBLICATIONS

Torreri et al., "Biomolecular interactions by Surface Plasmon Resonance technology", Ann 1st Super Sanita, 2005, pp. 437-441, vol. 41, No. 4.
Tran et al., "Association of Hereditary Heparin Co-Factor II Deficiency With Thrombosis", The LANCET, 1985, pp. 413-414, vol. 2.
Turpie, "The top 4 advances in antithrombotic care in the last year", Thrombosis Research, 2008, pp. S2-S6, vol. 123.
Verweij et al., "Paclitaxel (Taxol) and docetaxel (Taxotere): Not simply two of a kind", Annals of Oncology, 1994, pp. 495-505, vol. 5.
Vicente et al., "Antithrombotic activity of dermatan sulfate in heparin cofactor II-deficient mice", Blood, 2004, pp. 3965-3970, vol. 104, No. 13.
Vyavahare et al., "In vitro and in vivo evaluation of the site-specific administration of D-phenylalanyl-L-prolyl-L-arginyl chloromethyl ketone (PPACK): a powerful thrombin inhibitor", Journal of Controlled Release, 1993, pp. 165-173, vol. 27, No. 2.
Wallentin et al., "Ticagrelor versus Clopidogrel in Patients with Acute Coronary Syndromes", The New England Journal of Medicine, 2009, pp. 1045-1057, vol. 361, No. 11.
Weissmann et al., "Effect of melittin upon cellular and lysosomal membranes", Biochemical Pharmacology, 1969, pp. 1771-1775, vol. 18.
Weitz et al., "Clot-bound Thrombin is Protected from Inhibition by Heparin-Antithrombin III but is Susceptible to Inactivation by Antithrombin III-independent Inhibitors", Journal of Clinical Investigation, 1990, pp. 385-391, vol. 86.
Westrick et al., "Murine Models of Vascular Thrombosis", Arteriosclerosis, Thrombosis, and Vascular Biology, 2007, pp. 2079-2093, vol. 27.
Winter et al., "Molecular Imaging of Angiogenesis in Early-Stage Atherosclerosis With αvβ3-Integrin-Targeted Nanoparticles", Circulation, 2003, pp. 2270-2274, vol. 108.
Winter et al., "Molecular Imaging of Angiogenesis in Nascent Vx-2 Rabbit Tumors Using a Novel αvβ3-targeted Nanoparticle and 1.5 Tesla Magnetic Resonance Imaging", Cancer Research, 2003, pp. 5838-5843, vol. 63.
Winter et al., "Molecular Imaging by MRI", Current Cardiology Reports, 2006, pp. 65-69, vol. 8.
Winter et al., "Emerging nanomedicine opportunities with perfluorocarbon nanoparticles", Expert Rev. Med. Devices, 2007, pp. 137-145, vol. 4, No. 2.
Winter et al., "Antiangiogenic Synergism of Integrin-Targeted Fumagillin Nanoparticles and Atorvastatin in Atherosclerosis", JACC: Cardiovascular Imaging, 2008, pp. 624-634, vol. 1, No. 5.
Yamaoka et al., "Complementation Cloning of NEMO, a Component of the IκB Kinase Complex Essential for NF-κB Activation", Cell, 1998, pp. 1231-1240, vol. 93.
Zhou et al. "Suppression of inflammation in a mouse model of rheumatoid arthritis using targeted lipase-labile fumagillin prodrug nanoparticles", Biomaterials, 2012, pp. 8632-8640, vol. 33.
International Search Report and Written Opinion from related International Application No. PCT/US2014/36762, dated Oct. 9, 2014; 7 pgs.
International Search Report and Written Opinion from related International Application No. PCT/US2011/32744, dated Jul. 8, 2011; 10 pgs.
International Search Report and Written Opinion from related International Application No. PCT/US2010/61103, dated Apr. 6, 2011; 12 pgs.
International Search Report and Written Opinion from related International Application No. PCT/US2008/79414, dated Dec. 15, 2008; 15 pgs.
Ivey et al., "Thrombin regulates vascular smooth muscle cell proteoglycan synthesis via PAR-1 and multiple downstream signalling pathways", Thrombosis Research, 2008, pp. 288-297, vol. 123.
Kaiser et al., "Pharmacology of Synthetic Thrombin Inhibitors of the Tripeptide Type", Cardiovascular Drug Reviews, 1992, pp. 71-87, vol. 10, No. 1.

Kaneda et al., "Perfluorocarbon Nanoemulsions for Quantitative Molecular Imaging and Targeted Therapeutics", Ann Biomed Eng., 2009, pp. 1922-1933, vol. 37, No. 10.
Karin, "The Beginning of the End: IκB Kinase (IKK) and NF-κB Activation*", The Journal of Biological Chemistry, 1999, pp. 27339-27342, vol. 274, No. 39.
Karin et al., "NF-κB in Cancer: From Innocent Bystander to Major Culprit", Nature Reviews/Cancer, 2002, pp. 301-310, vol. 2.
Karin, "Nuclear factor-κB in cancer development and progression", Nature, 2006, pp. 431-436, vol. 441.
Kettner et al., "D-Phe-Pro-ArgCH2Cl-A Selective Affinity Label for Thrombin", Thrombosis Research, 1979, pp. 969-973, vol. 14, No. 6.
Kim et al., "Development of a novel dosage form for intramuscular injection of titrated extract of Centella asiatica in a mixed micellar system", International Journal of Pharmaceutics, 2001, pp. 141-147, vol. 220.
Klocek et al., "Thermodynamics of Melittin Binding to Lipid Bilayers. Aggregation and Pore Formation", Biochemistry, 2009, pp. 2586-2596, vol. 48, No. 12.
Kukreja et al., "The future of drug-eluting stents", Pharmacological Research, 2008, pp. 171-180, vol. 57.
Lanza et al., "Molecular Imaging of Stretch-Induced Tissue Factor Expression in Carotid Arteries with Intravascular Ultrasound", Investigative Radiology, 2000, pp. 227-234, vol. 35, No. 4.
Lanza et al., "Targeted Antiproliferative Drug Delivery to Vascular Smooth Muscle Cells With a Magnetic Resonance Imaging Nanoparticle Contrast Agent: Implications for Rational Therapy of Restenosis", Circulation, 2002, pp. 2842-2847, vol. 106.
Lanza et al., "Nanomedicine opportunities for cardiovascular disease with perfluorocarbon nanoparticles", Vanomedicine, 2006, pp. 321-329, vol. 1, No. 3.
Lee, "Anticoagulants in Coronary Artery Disease", Clinical Cardiology, 2008, pp. 615-628, vol. 26.
Lopez-Guerra et al., "NF-κB as a therapeutic target in chronic lymphocytic leukemia", Expert Opin. Ther. Targets, 2010, pp. 275-288, vol. 14, No. 3.
MacLean et al., "Hereditary and Acquired Antithrombin Deficiency: Epidemiology, Pathogenesis and Treatment options", Drugs, 2007, pp. 1429-1440, vol. 67, No. 10.
Marsh et al., "Molecular imaging with targeted perfluorocarbon nanoparticles: Quantification of the concentration dependence of contrast enhancement for binding to sparse cellular epitopes", Ultrasound Med Biol., 2007, pp. 950-958, vol. 33, No. 6.
May et al., "Selective Inhibition of NF-κB Activation by a Peptide That Blocks the Interaction of NEMO with the IκB Kinase Complex", Science, 2000, pp. 1550-1554, vol. 289.
May et al., "Individualized antithrombotic therapy in high risk patients after coronary stenting. A double-edged sword between thrombosis and bleeding", Journal of Thrombosis and Haemostasis, 2008, pp. 487-493, vol. 99.
Morawski et al., "Quantitative "Magnetic Resonance Immunohistochemistry" with Ligand-Targeted 19F Nanoparticles", Magnetic Resonance in Medicine, 2004, pp. 1255-1262, vol. 52.
Mulder et al., "MR molecular imaging and fluorescence microscopy for identification of activated tumor endothelium using a bimodal lipidic nanoparticle", The FASEB Journal, 2005, pp. 2008-2010, vol. 19.
Mulder et al., "Lipid-based nanoparticles for contrast-enhanced MRI and molecular imaging", NMR in Biomedicine, 2006, pp. 142-164, vol. 19.
Myerson et al., "'Thrombin sponge': A potent nanoparticle approach to inhibiting coagulation in cute thrombosis", The FASEB Journal, 2010, p. 574.2, vol. 24, No. 1.
Myerson et al., "Thrombin-inhibiting perfluorocarbon nanoparticles provide a novel strategy for treatment and magnetic resonance imaging of acute thrombosis", Journal of Thrombosis and Haemostasis, 2011, pp. 1292-1300, vol. 9, No. 7.
Office Action from related U.S. Appl. No. 13/641,252, dated Sep. 30, 2015; 20 pgs.
Office Action from related U.S. Appl. No. 13/641,252, dated Jun. 26, 2015; 11 pgs.

(56) References Cited

OTHER PUBLICATIONS

Office Action from related U.S. Appl. No. 12/682,098, dated Jun. 22, 2015; 27 pgs.
Office Action from related U.S. Appl. No. 12/682,098, dated May 9, 2013; 17 pgs.
Office Action from related U.S. Appl. No. 12/682,098, dated Jun. 11, 2012; 15 pgs.
Office Action from related U.S. Appl. No. 13/516,528, dated Sep. 14, 2015; 11 pgs.
Office Action from related U.S. Appl. No. 13/516,528, dated Dec. 9, 2014; 6 pgs.
Office Action from related U.S. Appl. No. 13/516,528, dated May 27, 2014; 7 pgs.
Office Action from related U.S. Appl. No. 13/516,528 dated Oct. 23, 2013; 20 pgs.
Office Action from related Japanese Patent Application No. 2013-505192, dated Jan. 15, 2015; 2 pgs.
Fourth Office Action from related Chinese Patent Application No. 200880117661.5, dated Jul. 25, 2013; 13 pgs.
Pan, et al., "Water Soluble Nano-Bialys: Preparation of a Vascularly Constrained, Slow Releasing Nano-Carrier for Hydrophilic and Hydrophobic Drugs", Oct. 2007, Abstract for presentation in American Chemical Society, Western Regional Meeting 2007, Frontiers in Chemistry, Biopharmaceuticals & Biotechnology.
Pan et al., "Lipid membrane editing with peptide cargo linkers in cells and synthetic nanostructures", The FASEB Journal, 2010, pp. 2928-2937, vol. 24, No. 8.
Pan et al., "Anti-Angiogenesis Therapy in the Vx2 Rabbit Cancer Model with Lipase-cleavable Sn 2 Taxane Phospholipid Prodrug using $\alpha v\beta 3$-Targeted Theranostic Nanoparticles", Theranostics, 2014, pp. 565-578, vol. 4, No. 6.
Partlow et al., "19F magnetic resonance imaging for stem/progenitor cell tracking with multiple unique perfluorocarbon nanobeacons", The FASEB Journal, 2007, pp. 1647-1654, vol. 21.
Pasparakis, "Regulation of tissue homeostasis by NF-κB signalling: implications for inflammatory diseases", Nature Reviews/Immunology, 2009, pp. 778-788, vol. 9.
Peters et al., "Targeting atherosclerosis by using modular, multifunctional micelles", PNAS, 2009, pp. 9815-9819, vol. 106, No. 24.
Petrasek et al., "Precise Measurement of Diffusion Coefficients using Scanning Fluorescence Correlation Spectroscopy", Biophysical Journal, 2008, pp. 1437-1448, vol. 94, No. 4.
Piras et al., "Polymeric nanoparticles for hemoglobin-based oxygen carriers", Biochimica et Biophysica Acta, 2008, pp. 1454-1461, vol. 1784.

\* cited by examiner

A

B

C

D

PARTICLES FOR IMAGING

CROSS REFERENCE TO RELATED APPLICATIONS

This application claims the priority of U.S. provisional application No. 60/981,192, filed Oct. 19, 2007, and U.S. provisional application No. 60/978,678, filed Oct. 9, 2007, each of which is hereby incorporated by reference in its entirety.

GOVERNMENTAL RIGHTS

The present invention was made, at least in part, with support by the National Institutes of Health Siteman Center of Cancer Nanotechnology Excellence grant number U54 CA119342. Accordingly, the United States Government may have certain rights in the invention.

FIELD OF THE INVENTION

The invention encompasses particles comprising metals and metallic compounds, and methods for using such particles to image biological tissue.

BACKGROUND OF THE INVENTION

Noninvasive molecular imaging and targeted drug delivery systems, often referred to as theranostic agents, are being developed to enable improved detection, patient risk stratification and site-specific treatment. There is a need in the art for the development of theranostic agents that may be used with a wide variety of imaging techniques, such as x-ray, CT, spectral CT (K-edge imaging), ultrasound, magnetic resonance, positron emission tomography, optical and photoacoustic tomographic imaging.

Spectral CT Imaging

Conventional CT uses x-rays to generate tomographical images of the x-ray absorption from the object under investigation. The dominating physical absorption effects are the so-called photoelectric effect and the Compton Effect. Both effects depend on the atomic number of the elements, the mass density and the energy. Biological tissue consists mostly of a mixture of elements with low atomic numbers. Only calcium has a somewhat larger atomic number and density. The contrast of CT is therefore dominated by the relative large contrast between air, soft tissue and bone (or other calcified objects). Different soft tissue types show only a limited contrast, which is usually directly coupled to density differences. CT contrast agents are based on dense elements with a high atomic number such as iodine. Earlier attempts to utilize the energy dependency of the absorption to improve the contrast in CT were technically successful but showed only limited clinical value. These so-called dual-energy techniques utilize the element dependent difference between the two dominating absorption effects to provide additional contrasts.

The measurement techniques of dual-energy CT provide only low energy resolution. This limitation can be overcome with advanced detector technology that provides good spectral resolution. Such detectors are based on photon counting devices with energy discrimination. Instead of just measuring the deposed energy of the entire x-ray beam, as it is done in conventional detectors, each individual photon is detected and its energy is measured. Spectral CT can improve the absorption contrast in CT to its physical limitations. Although better than conventional CT the added clinical value of spectral CT is limited, because the elementary composition of biological tissue does not yield strong differences in x-ray absorption.

This situation changes dramatically if spectral CT is used in combination with K-edge imaging. The photoelectric absorption contains some strong resonance effects at certain energies. If an x-ray photon contains enough energy to excite an electron in the K-shell, the absorption increases dramatically. The K-edge energy depends on the atomic number of the element. Some elements such as gadolinium, gold or bismuth have their K-edge in the x-ray energy band of CT. The spectral footprint of these elements combined with spectral CT detector technology provides unique imaging features. The high energy resolution of photon counting detectors and proper mathematical processing methods allow a complete separation of the attenuation from the K-edge material and the remaining elements. Spectral CT K-edge imaging can be seen as two simultaneous acquisitions where one is only sensitive to the K-edge material and the other is only conventional CT. Both imaging tasks (combined in a single real scan) provide separate images. The K-edge image shows only the K-edge material similar to PET or SPECT imaging where only the isotopes are visible. The other image shows a conventional CT image just without the K-edge material. It has been proven that the K-edge images deliver quantitative information of the K-edge material concentration.

Photo Acoustic Tomography

Photoacoustic tomography is a nonionizing imaging modality based upon differential absorption of electromagnetic waves for different tissue types. This imaging technique has attracted the attention of biomedical engineers for non invasive imaging. Photo Acoustic Tomography (PAT) is a materials analysis technique based on the reconstruction of an internal photoacoustic source distribution from measurements acquired by scanning ultrasound detectors over a surface that encloses the source under study. The PA source is produced inside the object by the thermal expansion that results from a small temperature rise, which is caused by the absorption of externally applied radiation of pulsed electromagnetic (EM) waves. This technique has great potential for applications in the biomedical field because of the advantages of ultrasonic resolution in combination with EM absorption contrast. PAT is also called optoacoustic tomography (OAT) or thermoacoustic tomography (TAT), with the term "thermoacoustic" emphasizing the thermal expansion mechanism in the PA generation. OAT refers particularly to light-induced PAT, while TAT is used to refer to rf-induced PAT.

Myocardial Infarction

Myocardial infarction is the leading cause of death for both men and women all over the world. As many as 200,000 to 300,000 people in the United States die each year before medical help is sought. Approximately 1.3 million cases of nonfatal myocardial infarction are reported for an annual incidence of approximately 600 per 100,000 people. Strikingly, around 300,000 Americans die from heart attacks each year before they reach a hospital. The proximate cause of myocardial infarction is coronary plaque rupture with thrombotic occlusion of blood supply.

Since the early work of Benson and Constantinides the acute formation of thrombus following atherosclerotic plaque rupture has been well recognized as the etiology of unstable angina, myocardial infarction, transient ischemic attacks and stroke. Although a myriad of medical advances in the detection and treatment of severe carotid and coronary artery stenosis have emerged, the most common source of thromboembolism remains rupturing vulnerable plaques that reside in vessels with only 50 to 60% residual stenosis. Sensitive detection and differentiation of vulnerable versus stable atherosclerotic plaques in vessels with mild severity stenosis remains limited with angiography, regardless of modality. Luminal imaging provides minimal information about arterial intimal pathology, and compensatory arterial remodeling to preserve lumen dimensions within diseased vessels further disguises the severity of atherosclerotic plaque burden.

A variety of approaches have emerged to detect vulnerable plaques based on intravascular ultrasound elastography, radionuclide imaging, and thermography, but magnetic resonance imaging (MRI) has emerged as a particularly sensitive modality to noninvasively visualize thromboses within the carotid artery. Unfortunately, wide excursions of the coronary vasculature during the cardiac cycle complicate routine MR coronary angiography and currently preclude MR molecular imaging of micro thrombus in the intimal microfissures of unstable plaque.

Multislice CT has emerged as the modality of choice for noninvasive coronary angiography (CTA). Current 16 and 64 slice scanners can generate contrast enhanced angiograms in 25 ms or less, and the eventual development of up to 256 slice scanners will permit complete acquisitions within one heart cycle. Although CTA, like MRA, is best for ruling out significant coronary disease, one expects that improved resolution of vascular detail will parallel faster data acquisitions and reduced blurring from partial volume dilution and motion artifacts. Yet, coronary calcium, a prominent feature of advanced atherosclerotic plaques and aging coronary vessels, will continue to present lumen assessment difficulties typically in suspect regions. Moreover, rapid multislice imaging will not detect intimal micro fissuring, and attenuation CT contrast agents, even if homed to thrombus features, will not be easily resolved from mural calcium deposits. Hence, there is a need in the art for improved imaging agents.

DETAILED DESCRIPTION OF THE INVENTION

Figure 1:
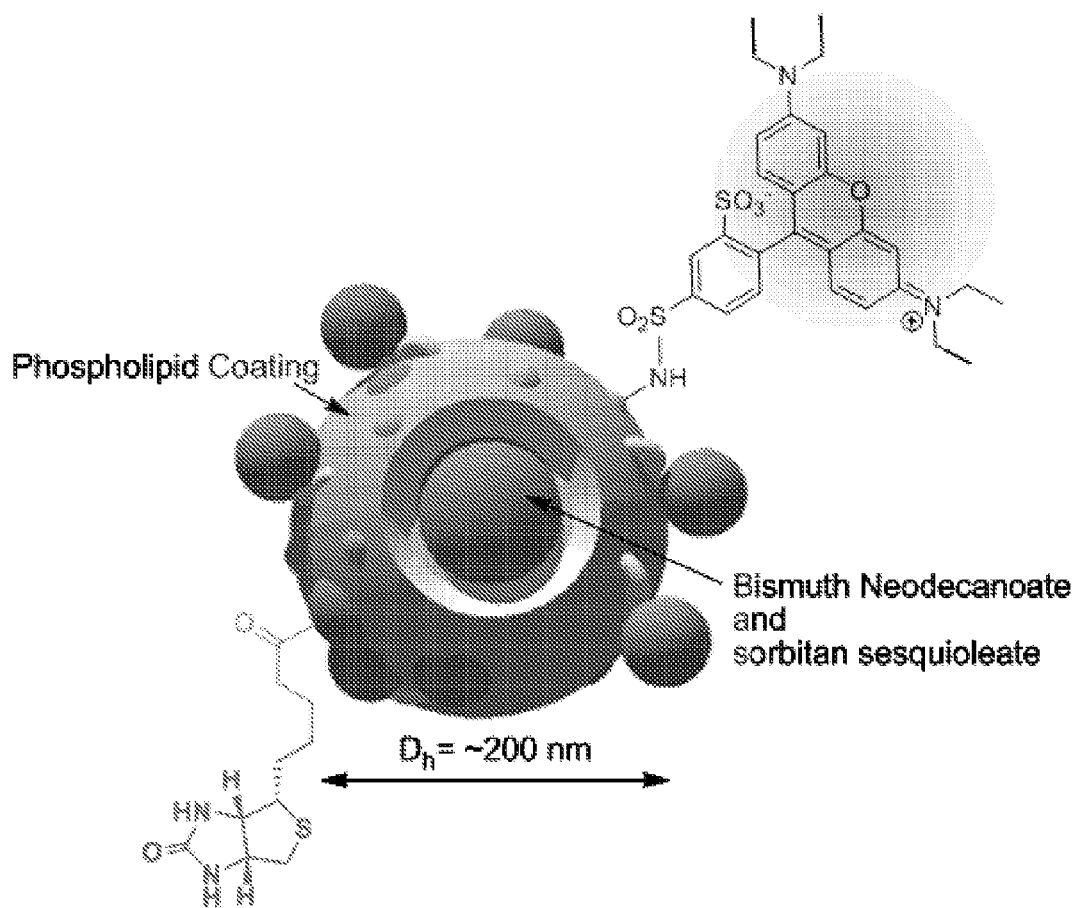
FIG. 1 depicts an illustration of a particle with a nominal diameter of 200 nm and an inner core comprising metal atoms.

The present invention provides a particle that may be used for imaging biological tissues. Generally speaking, the particle comprises an outer layer formed over an inner core. Advantageously, the inner core may comprise at least 1 metal atom, and may comprise 1,000,000 or more metal atoms.

I. Particle of the Invention

In some embodiments, the particle of the invention may be less than about 450 nm in nominal diameter. In alternative embodiments, the particle may be greater than about 450 nm in nominal diameter (e.g. for oral use). In several embodiments, the particle may be less than about 400 nm in nominal diameter. In other embodiments, the particle may be less than about 350 nm in nominal diameter. In certain embodiments, the particle may be between about 100 nm and about 400 nm in nominal diameter. In still other embodiments, the particle may be less than 100 nm in nominal diameter, e.g. less than 90 nm, less than 80 nm, less than 70 nm, less than 60 nm, or less than 50 nm. In one embodiment, the particle may be between about 150 nm and about 350 nm in nominal diameter. In another embodiment, the particle may be between about 200 nm and about 300 nm in nominal diameter. In certain embodiments, the size of the particle may constrain the biodistribution of the agent to the vasculature to enhance targeting specificity by precluding extravascular migration. For instance, if the same target is located both within and without of the vasculature, constraining the particle to the vasculature would reduce or eliminate accessibility to the ex-vasculature target. Generally speaking, the particle is spherical.

(a) Inner Core

Each particle of the invention has an inner core generally comprised of metal atoms and an oil or oil-like substance. Generally speaking, the inner core is liquid. Additionally, the inner core is typically soft and nonporous. However, at high metal concentrations, the inner core may have a high viscosity and high metal density. The inner core may be a solution, a mixture, or a suspension. In one embodiment, the inner core may be a solution. In another embodiment, the inner core may be a mixture. In yet another embodiment, the inner core may be a suspension. A non-limiting example of a suspension is a colloid.

i. Metal Atoms

In exemplary embodiments, the metal atoms of the particle are substantially located within the inner core of the particle. In certain embodiments, however, it is contemplated that the metal atoms may also be on the surface of the outer layer, within the outer layer, or any combination of the inner core or outer layer. For instance, the metal atoms may comprise part of the lipid head group of the outer layer, or may be encapsulated within the hydrophilic compartment of the outer layer. In one embodiment, the metal atoms are located both within the inner core of the particle and on the surface of the outer layer.

Typically, the inner core of the particle comprises at least 1 metal atom. In one embodiment, the inner core comprises at least 2 metal atoms, but less than 101 metal atoms. In another embodiments, the inner core comprises at least 100 metal atoms, but less than 1001 metal atoms. In yet another embodiment, the inner core comprises at least 1000 metal atoms, but less than 100,001 metal atoms. In still another embodiment, the inner core comprises at least 100,000 metal atoms. In some embodiments, the inner core comprises at least 150,000, at least 200,000, at least 250,000, at least 300,000, or at least 350,000 metal atoms. In other embodiments, the inner core comprises at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 metal atoms. In certain embodiments, the inner core comprises greater than about 1,000,000 metal atoms. In an alternative embodiment, the inner core comprises at least enough metal atoms to be an effective MRI, CT, spectral CT, ultrasound, PAT, or NIR/optical imaging agent. In another alternative, the inner core provides adequate metal for a detectable contrast-to-noise-ratio (CNR).

The metal atoms may generally be selected from the group of metal atoms comprised of metals with an atomic number of twenty or greater. For instance, in certain embodiments, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms.

The metal atoms that comprise the inner core of the particle may be metal ions. In some embodiments, the metal atoms may be in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $Pb^{2+}$, $Pb^{4+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal ions may comprise metal complexes, compounds, or chelates. For instance, the metal atoms may comprise a complex, chelate, or compound with diethylene triamine pentaacetic acid (DTPA), or tetramethyl heptanedionate (TMHD), 2,4-pentanedione, 1,4,7,10-tetraazacyclododecane-1,4,7,10-tetraacetic acid (DOTA), ethylenediaminetetraacetic acid disodium salt (EDTA), ethyleneglycol-O,O'-bis(2-aminoethyl)-N,N,N',N'-tetraacetic acid (EGTA), N-(2-hydroxyethyl)ethylenediamine-N,N',N'-triacetic acid trisodium salt (HEDTA), and nitrilotriacetic acid (NTA). These metal complexes, compounds, or chelates may be organo soluble or water-soluble.

As detailed above, in some embodiments, the metal atoms may comprise a metal compound. For instance, in certain embodiments, the inner core may comprise a plurality of metal compounds. Non-limiting examples of metal compounds may include metal oxides, metal sulphides, metal phosphates, metal carbonates, and metal chromates. Further examples may include organo-metal (or organometallic) compounds, organo-coated metal compounds, or spinels. In one embodiment, non-limiting examples of organometallic compounds may include metal polysorbate compounds, metal fatty acid compounds, metal surfactant compounds, metal aliphatic acid compounds, metal aromatic hydrophobic compounds, or combinations thereof. In another embodiment, non-limiting examples of organo-coated metal compounds may include metal fatty acid compounds, metal surfactant compounds, metal polymer compounds (including synthetic, natural, and semisynthetic polymer), metal aliphatic compounds, metal aromatic hydrophobic compounds, or combinations thereof.

In one embodiment, the metal atom may comprise a metal oxide. For instance, non-limiting examples of metal oxides may include iron oxide, manganese oxide, cobalt oxide, bismuth oxide, gold oxide, or gadolinium oxide. Additional examples may include magnetite, maghemite, or a combination thereof. In certain embodiments, the metal oxide may have the formula $MFe_2O_4$, where M is selected from the group comprising Fe, Mn, Co, Ni, Mg, Au, Cu, Zn, Ba, Sr Pt, Tl, Ti or a combination thereof. In various embodiments, the metal oxide is magnetic. In several embodiments, the inner core may comprise both a metal compound and an additional metal as described herein. For instance, the inner core may comprise a metal compound and an additional metal such as iodine, gadolinium, bismuth, or gold. Generally speaking, a metal compound of the invention is between about 1 and about 50 nm in diameter. For instance, a metal oxide may be about 1, 5, 10, 15, 20, 25, 30, 35, 40, 45, or 50 nm in diameter.

The inner core of the particle may comprise organo-soluble and/or water-soluble metal complexes. In certain embodiments, the inner core may comprise organo-soluble complexes of gadolinium, such as pentanedione-gadolinium (III). In other embodiments, the inner core may comprise organo-soluble complexes of bismuth, such as bismuthneodecanoate. In some embodiments, the inner core may comprise organo soluble complexes of gold, such as octane thiol coated gold.

In other embodiments, the inner core may comprise organometallic complexes of a metal. For instance, the inner core may comprise 2-ethylhexanoate-gold. In other embodiments, the inner core may comprise an organometallic complex of gadolinium, such as 2-ethylhexanoate gadolinium.

One skilled in the art would appreciate that the choice of metal is dictated, in part, by the imaging method used. Additionally, the choice of imaging method may dictate the size of the metal atom (or compound comprising a metal atom) and the oxidation state of the metal. In preferred embodiments for spectral CT, the metal atoms may be selected from the group comprising metals with an atomic number of 53 (i.e. iodine) to 83 (i.e. bismuth) and a K-edge in the x-ray energy band of CT. In preferred embodiments for MR, the metal atoms may have magnetic properties (e.g. paramagnetic or superparamagnetic properties). In preferred embodiments for optical or PAT imaging, the metal atoms may have NIR or optical emission properties. In preferred embodiments for ultrasound imaging, the metal atoms may have acoustic (i.e. sound) attenuation, absorbance, or scattering properties. In preferred embodiments for nuclear imaging, the metal atoms may have a radioactive particle emission, such as an alpha, beta, gamma, or positron emission. In certain embodiments, a metal that has radioactive particle emission may be artificially generated or naturally occurring.

ii. Inverted Micelles

Water-soluble metal complexes may be incorporated into the inner core as an agent enveloped within an inverted micelle. Generally speaking, the inverted micelles are formed from polymers covalently grafted with hydrophobic alkyl groups to form amphiphilic polymers. The polymers may be linear, branched, hyperbranched, dendritic, or star. Typically, the concentration of polymer is at least $10^{-6}$M. The less branched a polymer is, the lower the inverted micelle enveloping rates will be. In an exemplary embodiment, the polymers are hyperbranched. Generally speaking, hyperbranched refers to a polymer with greater than 60% branching. Suitable non-limiting examples of polymers include hyperbranched polyethylenimine, polylysines, and chitosans. For instance, generation 2-6 dendrimers, star polymers, or hyperbranched polyethylenimine with 19, 232, or 581 repeat units may be used.

Suitable non-limiting examples of hydrophobic alkyl groups that may be grafted onto the polymers include 10,12-pentacosadiynoic acid, hexadecyloctadecanoic acid, cholanic acid, linoleic acid, or palmitic acid. Methods of making inverted micelles from amphiphilic polymers and methods of enveloping metal complexes within inverted micelles are described in more detail in the Examples. Briefly, the hydrophobic polymers assume an inverted micelle about 5 to about 20 nm in size when vortexed in organic solvent. In some embodiments, the inverted micelle is about 5 to about 100 nm in size. In other embodiments, the inverted micelle is about 5 to about 50 nm in size. In still other embodiments, the inverted micelle is about 5 to about 25 nm in size. In a preferred embodiment, the inverted micelle is about 5 to about 15 nm in size.

The inverted micelles may also comprise guest compounds. These compounds may be imaging/tracking agents, or other desired molecules. For instance, non-limiting examples of guest compounds may include FITC, fluorescein-sodium, methyl orange, $GD^{3+}$-DTPA, Mn(III)-protoporphyrin chloride, p-SCN-Bz-DOTA, nanometer sized gold colloids, or doxorubicin. Generally speaking, drugs, dyes, chelates, or other molecules having comparable molecular weights and C-length as those guest compounds listed above may also comprise guest compounds of the inverted micelles.

iii. Oil or Oil-Like Substance

In addition to metal, the inner core of the particle may be comprised of oil or an oil-like substance. Generally speaking, the oil or oil-like substance should be non-toxic to the subject being imaged. In some embodiments, the oil may be a natural oil. Non-limiting examples of suitable natural oils may include peanut oil, olive oil, vegetable oil, safflower oil, almond oil, anise oil, bay oil, black pepper oil, bois de rose oil, rosewood, caraway oil, cardamom oil, cascara sagrada, castor oil, cedar leaf oil, thuja oil, celery seed oil, cinnamon bark oil, citronella oil, clove oil, cod liver oil, copaiba oil, coriander oil, corn oil, cottonseed oil, cumin oil, dillweed oil, eucalyptus oil, fennel oil, fir needle oil, garlic oil, ginger oil, grapefruit oil, juniper tar, lavender oil, N.F., lemon oil, lemongrass oil, lime oil, mandarin oil, olive oil, orange oil, origanum oil, palmarosa oil, peanut oil, peppermint oil, petitgrain oil, rose oil, rosemary oil, sage oil, sesame oil, soybean oil, and spearmint oil. In other embodiments, the oil or oil-like substance may be synthetic. Non-limiting examples may include sorbitans, such as polyoxyethylene sorbitan monooleate, polyoxyethylene sorbitan sesquioleate, polyoxyethylene sorbitan monopalmitate, polyoxyethylene sorbitan monolaureate, or polyoxyethylene sorbitan monostearate. In certain embodiments, the oil or oil-like substance may be semisynthetic. In various embodiments, the oil or oil-like substance may be a brominated oil, such as a brominated vegetable oil, a polysorbate, a spans, long- or medium-chain triglyceride lipid, a long- or medium-chain mixed mono- and di-glyceride, a surfactant, a mixed surfactant, a hydrophilic surfactant, polyoxyethylated/pegylated oil, polyoxyl 35 caster oil, PEG-15-hydroxystearate, solutol, medium chain glycerol, a PEG ester, labrasol, Tween 80, Tween 20, sucrose esters, sucrose monolaurate, tocopherol esters, or Vitamin E.

In certain embodiments, the inner core of the particle comprises an oil or oil-like substance and metal combination presented in Table A below. For an inner core that is comprised of inverted micelles, the oil oil-like substance used may be selected in part on the hydrophobic alkyl group used. In other words, the oil oil-like substance may be chosen in part based on the unsaturation present in the hydrophobic tail of the amphiphilic polymer. For instance, generally, peanut oil may be used for palmitate grafted polymers and safflower oil may be used for linoleate grafted polymers.

TABLE A

Certain metal and oil combinations for the inner core

| Metal | Oil or Oil-Like Substance |
|---|---|
| Gadolinium | Peanut oil |
| Gold | Peanut oil |
| Bismuth | Peanut oil |
| Gadolinium | Olive oil |
| Gold | Olive oil |
| Bismuth | Olive oil |
| Gadolinium | Vegetable oil |
| Gold | Vegetable oil |
| Bismuth | Vegetable oil |
| Gadolinium | Safflower oil |
| Gold | Safflower oil |
| Bismuth | Safflower oil |
| Gadolinium | polyoxyethylene sorbitan monooleate |
| Gold | polyoxyethylene sorbitan monooleate |
| Bismuth | polyoxyethylene sorbitan monooleate |
| Gadolinium | polyoxyethylene sorbitan sesquioleate |
| Gold | polyoxyethylene sorbitan sesquioleate |
| Bismuth | polyoxyethylene sorbitan sesquioleate |
| Gadolinium | polyoxyethylene sorbitan monopalmitate |
| Gold | polyoxyethylene sorbitan monopalmitate |
| Bismuth | polyoxyethylene sorbitan monopalmitate |

TABLE A-continued

Certain metal and oil combinations for the inner core

| Metal | Oil or Oil-Like Substance |
|---|---|
| Gadolinium | polyoxyethylene sorbitan monostearate |
| Gold | polyoxyethylene sorbitan monostearate |
| Bismuth | polyoxyethylene sorbitan monostearate |
| Gadolinium | polyoxyethylene sorbitan monostearate |
| Gold | polyoxyethylene sorbitan monostearate |
| Bismuth | polyoxyethylene sorbitan monostearate |

(b) Outer Layer

The particle generally comprises an amphiphilic material, and may also comprise one or more surfactants, one or more targeting agents, one or more bioactive agents, one or more imaging/tracking agents, or any combination thereof.

i. Amphiphilic Material

The particle of the invention comprises an outer layer comprised of amphiphilic material. The phrase "amphiphilic material," as used herein, refers to a material that has both a hydrophobic and a hydrophilic portion, such as lipid material or amphiphilic polymers. The amphiphilic material may be natural, synthetic, or semisynthetic. As used herein, "natural" refers to a material that may be found in nature, "synthetic" refers to a material that may be created in a laboratory setting, and "semisynthetic" refers to a nature material that has been altered in a laboratory setting. In one embodiment, the amphiphilic material is lipid material. For instance, the outer layer may be a single lipid layer or may include a multi-lamellar lipid layer. Lipid material is used herein in its broadest sense, including but not limited to a derivatized, natural, or synthetic phospholipid, a fatty acid, cholesterol, lysolipid, lipid, sphingomyelin, tocopherol, glucolipid, sterylamine, cardiolipin, plasmalogen, lipid with ether or ester linked fatty acids, a polymerized lipid, lipoprotein, glycolipids, derivatized surfactants, drug functionalized lipids, targeted ligand functionalized lipids, contrast agents conjugated lipids, lipid polymers, surfactants, or a combination thereof. The outer layer may also include lipid-conjugated polyethylene glycol (PEG).

Additionally, the outer layer may comprise a surfactant. Various commercial anionic, cationic, and nonionic surfactants may be employed, including Tweens, Spans, Tritons, and the like. In some embodiments, preferred surfactants are phospholipids and cholesterol. Other known surfactant additives such as PLURONIC F-68®, HAMPOSYL L30® (W.R. Grace Co., Nashua, N.H.), sodium dodecyl sulfate, Aerosol 413 (American Cyanamid Co., Wayne, N.J.), Aerosol 200 (American Cyanamid Co.), LIPOPROTEOL LCO® (Rhodia Inc., Manmmoth, N.J.), STANDAPOL SH 135® (Henkel Corp., Teaneck, N.J.), FIZUL 10-127® (Finetex Inc., Elmwood Park, N.J.), and CYCLOPOL SBFA 30® (Cyclo Chemicals Corp., Miami, Fla.) may also be used. Additionally, amphoterics, such as those sold with the trade names: DERIPHAT 170® (Henkel Corp.), LONZAINE JS® (Lonza, Inc.), NIRNOL C2N-SF® (Miranol Chemical Co., Inc., Dayton, N.J.), AMPHOTERGE W2® (Lonza, Inc.), and AMPHOTERGE 2WAS® (Lonza, Inc.) may be used. Additionally, non-ionic surfactants, such as those sold with the trade names PLURONIC F-68® (BASF Wyandotte, Wyandotte, Mich.), PLURONIC F-127® (BASF Wyandotte), BRIJ 35® (ICI Americas; Wilmington, Del.), TRITON X-100® (Rohm and Haas Co., Philadelphia, Pa.), BRIJ 52® (ICI Americas), SPAN 20® (ICI Americas), GENEROL 122 ES® (Henkel Corp.), TRITON N42® (Rohm and Haas Co.), TRITON N-101® (Rohm and Haas Co.), TRITON X-405® (Rohm and Haas Co.), TWEEN 80® (ICI Americas), TWEEN 85® (ICI Americas), BRIJ 56® (ICI Americas) and the like, may be used. Moreover, surfactants may include but are not limited to, 1,2-dipalmitoyl-sn glycerol-3-phosphoethanolamine-N-4-(p-maleimidophenyl)butyramide, amine-$PEG_{2000}$-phosphatidylethanolamine, phosphatidylethanolamine, acacia, cholesterol, diethanolamine, glyceryl monostearate, lanolin alcohols, lecithin, including egg-yolk lecithin, mono- and di-glycerides, mono-ethanolamine, oleic acid, oleyl alcohol, poloxamer, peanut oil, palmitic acid, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax. The above surfactants may be used alone or in combination to assist in stabilizing the particles.

Moreover, suspending and/or viscosity-increasing agents that may be used include, but are not limited to, acacia, agar, alginic acid, aluminum monostearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

In certain embodiments, the outer layer material (not including water) may comprise from about less than 1% to about 10% of the total volume of the particle. In a preferred embodiment, the outer layer material comprises about 2% of the total volume of the particle.

In another embodiment, the amphiphilic material is an amphiphilic polymer. In some embodiments, the amphiphilic material may contain both hydrophilic and hydrophobic blocks. For instance, the hydrophilic block may be polyacrylic acid. In certain embodiments, the hydrophobic block may be polysterene, polymethyl acrylate or polyisoprene. Amphiphilic polymers of the present invention may also contain, as polymerized units, from zero to 50% of one or more vinyl or vinylidene monoaromatic monomers. Suitable vinyl or vinylidene monoaromatic monomers may include, for example, styrene, and styrene that is substituted on the aromatic ring with one or more (C1-C4)alkyl radicals, hydroxyl radicals, chlorine atoms or bromine atoms. When present, the vinyl or vinylidene monoaromatic monomer is preferably styrene, α-methyl styrene or chlorostyrene. Polymers of the present invention may also optionally contain, as polymerized units, from zero to 50%, one or more other copolymerizable monomers. Suitable copolymerizable monomers may include, for example, butadiene, acrylonitrile, ethylene, vinyl acetate, hydroxyalkyl (meth)acrylates, (C5-C20)alkyl (meth)acrylates, poly(alkyleneoxide) di(meth)acrylates, amides of ethylenically unsaturated (C3-C6) carboxylic acids, amides of ethylenically unsaturated (C3-C6)carboxylic acids that are substituted at the nitrogen by one or two (C1-C4)alkyl groups, acrylamide, methacrylamide, N-methylol (meth)acrylamide, quaternary ammonium salts of acrylamide, (3-acrylamidopropyl)trimethylammonium chloride, (3-methacrylamidopropyl)trimethylammonium chloride, quaternary ammonium salts of (meth)acrylate esters (such as 2-(N,N,N-trimethylammonium)ethyl (meth)acrylate), 2-(dimethylamino)ethyl (meth)acrylate, N,N-dimethyl-N-methylacryloxyethyl-N-(3-sulfopropyl)-ammonium betaine and N,N-dimethyl-N-acrylamidopropyl-N-(3-sulfopropyl)-ammonium betaine. Additional suitable copolymerizable monomers may include, for example, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propene-1-sulfonic acid, styrene sulfonic acid, vinylsulfonic acid, 3-sulfopropyl acrylate, 3-sulfopropyl methacrylate, sulfomethyl acrylamide and sulfomethyl methacrylamide.

In various embodiments, the amphiphilic material of the outer layer may be cross-linked to stabilize the particle. The cross-linking may enhance stability of the particle, as well as the integrity of the particle, and may improve retention of the inner core within the particle. In some embodiments, the particles may be cross-linked on the surface of the outer layer. In other embodiments, the particles may be cross-linked within the outer layer. The cross-linking may be chemical cross-linking or photochemical cross-linking. Briefly, suitable cross-linkers will react with one or more active groups of the outer layer. Cross-linkers may be homobifunctional or heterobifunctional. Suitable chemical cross-linkers may include glutaraldehyde, bis-carboxylic acid spacers, or bis-carboxylic acid-active esters. Additionally, the outer layer may be chemically cross-linked using a bis-linker amine/acid by carbodiimide coupling protocol. Alternatively, the particle may be cross-linked using a click chemistry protocol. In still other embodiments, carbodiimde-coupling chemistry, acylation, active ester coupling, or alkylation may be used to cross-link the outer layer. In an exemplary embodiment, the cross-linking is carbodiimide mediated. In some embodiments, EDC (also EDAC or EDCl, 1-ethyl-3-(3-dimethylaminopropyl) carbodiimide hydrochloride), a highly water soluble carbodiimide, is employed in the 4.0-6.0 pH range to activate carboxyl groups for the coupling of primary amines to yield amide bonds. To enhance the coupling efficiencies, EDC may be used in combination with N-hydroxysuccinimide (NHS) or sulfo-NHS. One of ordinary skill in the art would recognize that a suitable cross-linker can and will vary depending on the composition of the particle and the intended use.

In addition to amphiphilic material and surfactants, the outer layer may also include targeting agents, bioactive agents, imaging/tracking agents, or a combination thereof. Such a combination, in conjunction with lipid material, is referred to herein as an outer layer component co-mixture.

ii. Targeting Agents

In some embodiments, the outer layer of the particle may further comprise targeting agents, such that particles comprising targeting agents may be delivered and concentrated at desired sites. Targeted particles may include a wide variety of targeting agents in the outer layer, including but not limited to, antibodies, antibody fragments, proteins, peptides, carbohydrates, lipids, small molecules, polysaccharides, nucleic acids, aptamers, peptidomimetics, other mimetics and drugs alone or in combination. Additionally, targeting agents may include microbes, such as phage or viruses. A targeting agent may also be an engineered analogue or derivate of each of the above. Targeting agents may be utilized to specifically bind the particles to cellular epitopes and receptors, and may be attached directly or indirectly to the particle.

Direct conjugation of the targeting agents to the particles refers to the preparation of a targeting agent-particle complex wherein the targeting agent is either adsorbed through ionic, electrostatic, hydrophobic or other noncovalent means to the particle surface (e.g. acylated-antibody, or hybridization between complementary nucleic acid sequences), or chemically linked to the surface through covalent bonds to a component of the lipid surface, or intrinsically incorporated into the lipid surfactant membrane as a component of the membrane (e.g. a lipid derivatized to a peptidomimetic agent).

Indirect conjugation refers to forming the complex between the particle and the targeting agent in vivo in two or more steps. Indirect conjugation utilizes a chemical linking system to produce the close and specific apposition of the particle to a targeted cell or tissue surface. A non-limiting example of an indirect targeting system is avidin-biotin.

Avidin-biotin interactions are useful noncovalent targeting systems that have been incorporated into many biological and analytical systems and selected in vivo applications. Avidin has a high affinity for biotin ($10^{-15}$ M) facilitating rapid and stable binding under physiological conditions. Targeted systems utilizing this approach are administered in two or three steps, depending on the formulation. Typically, a biotinylated ligand, such as a monoclonal antibody, is administered first and "pretargeted" to the unique molecular epitopes. Next, avidin is administered, which binds to the biotin moiety of the "pretargeted" ligand. Finally, the biotinylated particle is added and binds to the unoccupied biotin-binding sites remaining on the avidin thereby completing the biotinylated ligand-avidin-particle "sandwich". The avidin-biotin approach can avoid accelerated, premature clearance of targeted particles by the mononuclear phagocyte system (MPS) secondary to the presence of surface antibody. Additionally, avidin, with four independent biotin-binding sites provides signal amplification and improves detection sensitivity.

Targeting agents may be chemically attached to the surface of particles by a variety of methods depending upon the nature of the targeting agent and composition of the particle surface. Direct chemical conjugation of targeting agents to proteinaceous particles often take advantage of numerous amino-groups (e.g. lysine) inherently present within the surface. Alternatively, functionally active chemical groups such as pyridyldithiopropionate, maleimide or aldehyde may be incorporated into the surface as chemical "hooks" for targeting agent conjugation after the particles are formed. Another common post-processing approach is to activate surface carboxylates with carbodiimide prior to targeting agent addition.

The selected covalent linking strategy is primarily determined by the chemical nature of the targeting agent. For instance, monoclonal antibodies and other large proteins may denature under harsh processing conditions whereas the bioactivity of carbohydrates, short peptides, aptamers, drugs or peptidomimetics often can be preserved under these conditions.

To ensure high targeting agent binding integrity and maximize targeted particle avidity flexible spacer arms, e.g. polyethylene glycol, amino acids, long or short chain hydrocarbons, sugars (e.g. polydextrose), nucleic acids, aptamers, or simple caproate bridges, can be inserted between an activated surface functional group and the targeting agent. These extensions may be 2 nm or longer and may minimize interference of targeting agent binding by particle surface interactions.

The targeting agent may be immobilized within the lipid material by using a "primer material". A "primer material" is any surfactant compatible compound incorporated in the particle to chemically couple with or adsorb a specific binding or targeting agent i.e. any constituent or derivatized constituent incorporated into the outer layer that could be chemically utilized to form a covalent bond between the particle and targeting ligand or a component of the targeting ligand (if it has subunits). The targeting agent may be covalently bonded to "primer material" with coupling agents using methods that are known in the art. One type of coupling agent may use a carbodiimide such as 1-ethyl-3-(3-N,N dimethylaminopropyl)carbodiimide hydrochloride or 1-cyclohexyl-3-(2-morpholinoethyl)carbodiimide methyl-p-toluenesulfonate. The primer material may be amine-$PEG_{2000}$-phosphatidylethanolamine, phosphatidylethanolamine, N-caproylamine phosphatidylethanolamine, N-dodecanylamine phosphatidylethanolamine, phosphotidylthioethanol, 1,2-diacyl-sn-glycerol-3-phosphoethanolamine-N-[4-p-maleimidephenyl)-butyr amide, N-succinyl-phosphatidylethanolamine, N-glutaryl-phosphatidylethanolamine, N-dodecanyl-phosphatidylethanolamine, N-biotinyl-phosphatidylethanolamine, N-biotinylcaproyl-phosphatidylethanolamine, and phosphatidylethylene glycol. Other suitable coupling agents may include aldehyde coupling agents having either ethylenic unsaturation such as acrolein, methacrolein, or 2-butenal, or having a plurality of aldehyde groups such as glutaraldehyde, propanedial or butanedial. Other coupling agents may include 2-iminothiolane hydrochloride and bifunctional N-hydroxysuccinimide esters such as disuccinimidyl subsrate, disuccinimidyl tartrate, bis[2-(succinimidooxycarbonyloxy)ethyl]sulfone, disuccinimidyl propionate, and ethylene glycolbis(succinimidyl succinate). Non-limiting examples of heterobifunctional reagents may include N-(5-azido-2-nitrobenzoyloxy) succinimide, p-azidophenylbromide, p-azidophenylglyoxal, 4-fluoro-3-nitrophenylazide, N-hydroxysuccinimidyl-4-azidobenzoate, m-maleimidobenzoyl N-hydroxysuccinimide ester, methyl-4-azidophenylglyoxal, 4-fluoro-3-nitrophenyl azide, N-hydroxysuccinimidyl-4-azidobenzoate hydrochloride, p-nitrophenyl 2-diazo-3,3,3-trifluoropropionate, N-succinimidyl-6-(4'-azido-2'-nitrophenylamino)hexanoate, succinimidyl 4-(N-maleimidomethyl)cyclohexane-1-carboxylate, succinimidyl 4-(p-maleimidophenyl)butyrate, N-succinimidyl(4-azidophenyldithio)propionate, N-succinimidyl 3-(2-pyridyldithio)propionate, and N-(4-azidophenylthio)phthalamide. Non-limiting examples of homobifunctional reagents may include 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. Covalent bonding of a specific binding species to the "primer material" can be carried out with the above reagents by conventional, well-known reactions, for example, in the aqueous solutions at a neutral pH and at temperatures of less than 25° C. for 1 hour to overnight.

iii. Bioactive Agents

The outer layer of the particles of the invention may incorporate bioactive agents (e.g. drugs, therapeutic compounds, genetic materials, metals (such as radioactive isotopes), proteins, peptides, carbohydrates, lipids, steroids, nucleic acid based materials, or derivatives, analogues, or combinations thereof) in their native form or derivatized with hydrophobic or charged moieties to enhance incorporation or adsorption to the particle. Such bioactive agents may be water soluble or may be hydrophobic. Generally speaking, bioactive agents may be accessible on the surface of the outer layer or they may be embedded in the outer layer. In certain embodiments, the bioactive agent may be located in the inner core of the particle. Non-limiting examples of bioactive agents may include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. Non-limiting examples of bioactive agents are included in Table B below. Additionally, a particle of the invention may include two or more, three or more, or four or more bioactive agents.

TABLE B

Non-limiting Examples of Bioactive Agents

| Bioactive Agent | Non-limiting examples |
|---|---|
| Immune-related agents | immune serums, antitoxins, antivenoms bacterial vaccines, viral vaccines, rabies prophylaxis products |
| thyroid agents | iodine products and anti-thyroid agents |
| respiratory products | xanthine derivatives theophylline and aminophylline |
| antineoplastic agents | platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon α-2a, interferon α-2b, teniposide (VM-26), vinblastine sulfate (VLB), vincristine sulfate, bleomycin sulfate, hydroxyurea, procarbazine, and dacarbazine |
| anti-helmintics | pyrantel pamoate, piperazine, tetrachloroethylene, thiabendazole, niclosamide |
| antimalarials | Chloroquine, amodiaquine, antifolate drugs, proguanil (chloroguanide), mefloquine, quinine, halofantrine, artemesinin and derivatives, primaquine, doxycycline, tetracycline, and clindamycin |
| mitotic inhibitors | etoposide, colchicine, and the vinca alkaloids |
| hormones | androgens, progestins, estrogens and antiestrogens, growth hormone, melanocyte stimulating hormone, estradiol, beclomethasone dipropionate, betamethasone, betamethasone acetate and betamethasone sodium phosphate, |

TABLE B-continued

Non-limiting Examples of Bioactive Agents

| Bioactive Agent | Non-limiting examples |
|---|---|
|  | vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, glucagon and their derivatives |
| antiprotozoans | chloroquine, hydroxychloroquine, metronidazole, quinine and meglumine antimonite |
| antituberculars | para-aminosalicylic acid, isoniazid, capreomycin sulfate cycloserine, ethambutol hydrochloride ethionamide, pyrazinamide, rifampin, and streptomycin sulfate |
| cardiovascular products | chelating agents and mercurial diuretics and cardiac glycosides |
| blood products | parenteral iron, hemin, hematoporphyrins and their derivatives |
| biological response modifiers | muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine |
| anti-fungal agents | ketoconazole, nystatin, griseofulvin, flucytosine (5-fc), miconazole, amphotericin B, ricin, cyclosporins, and β-lactam antibiotics (e.g., sulfazecin) |
| vitamins | cyanocobalamin neinoic acid, retinoids and derivatives such as retinol palmitate, and α-tocopherol |
| peptides | manganese super oxide dismutase; enzymes such as alkaline phosphatase |
| anti-allergic agents | Amelexanox |
| anti-coagulation agents | phenprocoumon and heparin |
| circulatory drugs | Propranolol |
| metabolic potentiators | Glutathione |
| antivirals | acyclovir, amantadine azidothymidine (AZT, DDI, Foscarnet, or Zidovudine), ribavirin and vidarabine monohydrate (adenine arabinoside, ara-A) |
| antianginals | diltiazem, nifedipine, verapamil, erythritol tetranitrate, isosorbide dinitrate, nitroglycerin (glyceryl trinitrate) and pentaerythritol tetranitrate |
| antibiotics | dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin, aminoglycosides and tetracycline |
| antiinflammatories | diflunisal, ibuprofen, indomethacin, meclofenamate, mefenamic acid, naproxen, oxyphenbutazone, phenylbutazone, piroxicam, sulindac, tolmetin, aspirin and salicylates |

TABLE B-continued

Non-limiting Examples of Bioactive Agents

| Bioactive Agent | Non-limiting examples |
|---|---|
| antirheumatics | Adalimumab, azathioprine, chloroquine and hydroxychloroquine (antimalarials), cyclosporine (Cyclosporin A), D-penicillamine, etanercept, gold salts (sodium aurothiomalate, auranofin), infliximab, leflunomide, methotrexate, minocycline (a tetracycline antibiotic), sulfasalazine |
| narcotics | Paregoric, opiates, codeine, heroin, methadone, morphine and opium |
| cardiac glycosides | deslanoside, digitoxin, digoxin, digitalin and digitalis |
| neuromuscular blockers | atracurium mesylate, gallamine triethiodide, hexafluorenium bromide, metocurine iodide, pancuronium bromide, succinylcholine chloride (suxamethonium chloride), tubocurarine chloride and vecuronium bromide |
| sedatives (hypnotics) | amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam |
| local anesthetics | bupivacaine hydrochloride, chloroprocaine hydrochloride, etidocaine hydrochloride, lidocaine hydrochloride, mepivacaine hydrochloride, procaine hydrochloride and tetracaine hydrochloride |
| general anesthetics | droperidol, etomidate, fentanyl citrate with droperidol, ketamine hydrochloride, methohexital sodium and thiopental sodium |
| radioactive particles or ions | strontium, iodide rhenium, yttrium, and radiopharmaceuticals, such as radioactive iodine and phosphorus product |

In some embodiments, a bioactive agent may also be a targeting agent. For instance, an antibody, peptide fragment, or a mimetic of a biologically active ligand may be a bioactive agent, such as an antagonist or agonist, when bound to specific epitopes. As an example, antibody against $\alpha v\beta 3$ integrin on neovascular endothelial cells has been shown to transiently inhibit growth and metastasis of solid tumors. Thus, in another embodiment of the invention, the targeting agent and bioactive agent may be constituted by a single component which functions both to target the particle and to provide the bioactive agent to the desired site.

iv. Other Imaging/Tracking Agents

The outer layer of a particle of the invention may also include other imaging/tracking agents. For instance, the outer layer may include imaging/tracking agents that may be used for microscopy, e.g. fluorescent microscopy, confocal microscopy, or electron microscopy, magnetic resonance imaging, tomography, such as gamma (SPECT/CT, planar) and positron emission tomography (PET/CT), radiography, or ultrasound. Imaging/tracking agents may be detectable in situ, in vivo, ex vivo, and in vitro. Microscopy imaging/tracking agents are well known in the art, and may include fluorescent molecules such as FITC, rhodamine, and Alexafluor cyan dyes. Similarly, magnetic resonance imaging molecules, radiography imaging molecules, near infrared (NIR) and ultrasound molecules are well known in the art, and an appropriate imaging molecule may be selected by one of skill in the art after consideration of the composition of the particle and the intended use of the particle. In certain embodiments, the outer layer may also comprise chelators for radiometals to be detected by nuclear imaging methods, such as PET, SPECT, and related methodologies.

v. Outer Layer Component Co-Mixtures

As described above, an outer layer component co-mixture may comprise lipid material, and may optionally comprise one or more surfactants, one or more targeting agents, one or more imaging/tracking agents, one or more bioactive agents, or any combination thereof.

In one embodiment, an outer layer component co-mixture may comprise about 50 to about 95 mole % egg yolk lecithin, about 0 to about 1 mole % 1,2-dipalmitoyl-sn glycero-3-phosphoethanolamine-N-4-(p-maleimidophenyl) butyramide and/or amine-PEG2000-phosphatidylethanolamine, about 2 mole % phosphatidylethanolamine, and about 0 to about 20 mole % cholesterol. In another embodiment, an outer layer component co-mixture may comprise about 61 mole % egg yolk lecithin, about 1 mole % biotinylated-phosphatidylethanolamine, about 8 mole % cholesterol, and about 30 mole % gadolinium-DTPA-BOA. In yet another embodiment, an outer layer component co-mixture may comprise about 90 mole % egg yolk lecithin, about 1 mole % biotinylated-phosphatidylethanolamine, and about 9 mole % cholesterol. In still another embodiment, an outer layer component co-mixture may comprise about 89 mole % egg yolk lecithin, about 1 mole % biotinylated-phosphatidylethanolamine, and about 10 mole % cholesterol.

(c) Process for Preparing Particles

Generally speaking, the particles of the invention may be produced by high shear mixing of the outer layer components with the inner core components. Non-limiting examples of high-shear mixing may include microfluidization, sonication, homogenization, or related mixing. Typically, about 15% to about 25% v/v of the inner core components (e.g. oil and organo and/or water soluble metal) are combined with about 1% to about 4% w/v outer layer component co-mixture, about 0 to about 3% glycerin, and the remaining balance, if any, with water. The resulting mixture is blended and then microfluidized. Particle size may be determined by methods known in the art, for instance, with a laser light-scattering submicron particle size analyzer.

In one embodiment, a particle of the invention is produced by microfluidizing a gadolinium-polymer-oil mixture (20% v/v), a outer layer component co-mixture (2.0%, w/v), glycerin (1.7%, w/v), and water for the balance. In another embodiment, a particle of the invention is produced by microfluidizing a bismuth neodecanoate-oil mixture (20% v/v), a outer layer component co-mixture (2.0%, w/v), glycerin (1.7%, w/v), and water for the balance. In yet another embodiment, a particle of the invention may be produced by microfluidizing a colloidal gold nanoparticle-polymer-oil mixture (20% v/v), a outer layer component co-mixture (2.0%, w/v), glycerin (1.7%, w/v), and water for the balance. In still another embodiment, a particle of the invention may be produced by micro fluidizing a hydrophobically coated gold-oil mixture (20% v/v), a outer layer component co-mixture (2.0% w/v), glycerin (1.7%, w/v), and water for the balance.

Methods of microfluidization are well known in the art, as illustrated in the Examples.

(d) Particle Properties

The size and shape of the particles can and will vary without departing from the scope of the present invention. For example, the particles may be spherical, regularly shaped, irregular, or combinations thereof. Generally, their size may be measured in terms of their hydrodynamic diameter. The characteristic diameter of a particle may be estimated, for example, by light scattering experiments.

Typically, the particle, when used for imaging, provides a useable contrast-to-noise-ratio (CNR). In some embodiments, the particle provides a minimum of about 30, 31, 32, 33, 34, 35, 36, 37, 38, 39, 40, 41, 42, 43, 44, 45, 46, 47, 48, 49, or 50 µM metal/voxel for a minimum CNR of 3.

In some embodiments, a particle of the invention may have a zeta potential in deionized water of about −10 mV to about −60 mV. For instance, a particle of the invention may have a zeta potential of about −10, −11, −12, −13, −14, −15, −16, −17, −18, −19, −20, −21, −22, −23, −24, −25, −26, −27, −28, −29, −30, −31, −32, −33, −34, or −35 mV.

II. Composition of Particles

Typically, the particles of the invention are formulated as a composition for in vivo use. In exemplary embodiments, the composition is formulated for parental use. The size of particles utilized in a composition will vary depending upon the composition of the particle, e.g. the metal used. In one embodiment, 70% or more of the particles in such a composition may be less than about 450 nm in hydrodynamic diameter. In another embodiment, 75%, 80%, 85%, or 90% or more of the particles in such a composition may be less than about 450 nm in hydrodynamic diameter. In certain embodiments, 70%, 75%, 80%, 85%, 90% or 95% or more of the particles in such a composition may be between about 150 nm and about 350 nm in hydrodynamic diameter. In an alternative embodiment, 70%, 75%, 80%, 85%, 90% or 95% or more of the particles in such a composition may be constrained to the vasculature by their size.

A composition comprised of a plurality of particles may be a solution, a mixture, or a suspension. In one embodiment, the composition may be a solution. In another embodiment, the composition may be a mixture. In another embodiment, the composition may be a suspension. A non-limiting example of a suspension is a colloid.

In some embodiments, the composition may be a colloid. Generally speaking a colloid is a suspension of fine particles that do not readily settle out of the suspension. A colloid may be formed by microfluidization, as described in section I(d) above.

A composition of the particles of the invention may be administered to a subject to enable imaging and/or treatment of biological tissue. Suitable subjects include, but are not limited to, mammals, amphibians, reptiles, birds, fish, and insects. Non-limiting examples of mammals include humans, non-human primates, and rodents.

The composition may be formulated and administered to a subject by several different means that will deliver an effective dose for imaging. Such compositions may generally be administered parenteraly, intraperitoneally, intravascularly, or intraplumonarily in dosage unit formulations containing conventional nontoxic pharmaceutically acceptable carriers, adjuvants, excipients, and vehicles as desired. The term parenteral as used herein includes topical, subcutaneous, intravenous, intramuscular, intraperitoneal, intracystic, intrauterine, intraauricular, intranasal, ocular, intraocular, intrapulmonary, oral, intrapharyngeal, transrectal, intra or transurethral, intrauterine, intravaginal, or intrasternal injection or infusion. Additionally, the term parenteral includes spraying or aerosol administration techniques. In one embodiment, the composition may be administered in a bolus. In a preferred embodiment, the composition may be administered intravenously. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful. For imaging purposes, formulations for parenteral administration may be in the form of biocompatible solutions or suspensions. Other adjuvants and modes of administration are well and widely known in the pharmaceutical art.

One of skill in the art will recognize that the amount and concentration of the composition administered to a subject for imaging will depend in part on the subject and the tissue to be imaged. Methods for determining optimal amounts are known in the art, and more details may be found in the Examples.

III. Imaging Biological Tissue

A composition of the invention may be used to image biological tissue. The imaging may be performed in situ, in vitro, ex vivo, or in vivo. Suitable imaging techniques to be used in conjunction with compositions of the invention may include CT imaging, spectral CT imaging (K-edge imaging), radiography, nuclear imaging (e.g. PET), near infra red (NIR), optical, ultrasound, magnetic resonance (MR) imaging (including nuclear magnetic resonance), photoacoustic tomographic (PAT) imaging, acoustic optical imaging, x-ray imaging and combinations thereof. Advantageously, particles of the invention may be used in multi-modality imaging. In addition, particles of the invention may be used for both steady-state acquisition and first pass acquisition. In one embodiment, a particle of the invention may be used for both T1 and T2 imaging. A particle of the invention may be simultaneously used for imaging and bioactive agent delivery, imaging alone, or bioactive agent delivery alone.

Generally speaking, the method for obtaining an image of a biological tissue of a subject comprises administering a composition comprising a plurality of particles, as described in section II above, performing a signal acquisition scan on the subject, and processing the data from the signal acquisition to form an image of the subject. Methods of performing a signal acquisition scan and processing the data to form an image are known in the art. In one embodiment, the method may further comprise generating data from the signal acquisition scan other than an image that is relevant to the subject. In another embodiment, the method further comprises processing the data and generated images for interpretations relevant to the subject.

In an embodiment for obtaining a spectral CT image of a biological tissue of a subject, the method comprises administering a composition of the invention, as described in section II above, performing a spectral CT scan on the subject, and processing the data from the scan so as to form a spectral CT image of the subject. Similarly, the method for obtaining an MRI image of a biological tissue of a subject comprises administering a composition of the invention, as described in section II above, performing an MRI scan on the subject, and processing the data from the scan so as to form a MR image. Similarly, the method for obtaining an PAT or INR-optical image of a biological tissue of a subject comprises administering a composition of the invention, as described in section II above, performing an PAT or optical scan on the subject, and processing the data from the scan so as to form a an image.

In certain embodiments, the image is made with an optical, fluorescent, electron, confocal, or acoustic atomic force microscopes.

Tissue, as used herein, may refer to cells, organs, tumors, or material associated with cells, organs, or tumors, such as blood clots. Suitable tissues may include, but are not limited to, heart, lungs, brain, eye, stomach, spleen, bones, pancreas, gall bladder, kidneys, liver, intestines, skin, uterus, bladder, eyes, lymph nodes, blood vessels, and blood and lymph components. A non-limiting example of blood components is a microthrombus. In some embodiments, a particle of the invention may be used to image angiogenesis. In other embodiments, a particle of the invention may be used for volume imaging in a biological tissue. For instance, a particle of the invention may be used for volume imaging in a blood vessel, bladder, bowel, or other body cavity. In certain embodiments, a biological tissue may comprise a biomarker that the particle is targeted to. For instance, in some embodiments, a biomarker may comprise a component of a microthrombus, blood, blood vessel, lymph vessel, or extravascular vessel.

A tissue or biomarker may be associated with a pathology or disease. For instance, a tissue or biomarker may be associated with an oncologic, cardiovascular, dermatological, urogenital, pulmonary, muscular skeletal, gastrointestinal, neurological, hematologic, endocrine, sensory organ, inflammatory or rheumatologic diseases.

Regardless of the type of imaging used, the metal comprising the particles should be appropriate for the selected imaging type. For instance, for CT imaging, the metal should be selected from the group of metals consisting of metals that have a K-edge within the x-ray energy band of CT. Additionally, the amount of metal that comprises the particle can and will vary depending on the intended method of imaging. For instance, see Table C below.

| IMAGING METHOD | NUMBER OF METAL ATOMS |
| --- | --- |
| CT imaging | Between about 300,000 to about 1,000,000. In exemplary embodiments, greater than 500,000. |
| spectral CT imaging | Between about 300,000 to about 1,000,000 atoms, In exemplary embodiments, greater than 500,000 |
| near infra red (NIR) | Between about 1 to about 1,000,000 atoms |
| Optical or photoacoustical | Between about 1 to about 1,000,000 atoms |
| ultrasound | Between about 1 to about 1,000,000 atoms |
| magnetic resonance (MR) imaging | About 100,000 atoms |

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpretated as illustrative and not in a limiting sense.

EXAMPLES

The following examples illustrate various iterations of the invention.

Example 1

Synthesis and Characterization of Gadolinium Particles

Synthesis of Gadolinium Based Particles

A prototype particle with a nominal hydrodynamic diameter between 180-250 nm with a payload of 300,000 to 500,000 gadolinium atoms per bound particle has been prepared. These particles incorporate an amphiphilic, hyperbranched cationic polymer that is complexed noncovalently to DTPA-gadolinium chelates to form ~10 nm sized inverted micelles. These inverted micelles are suspended in oil to form a homogenous, transparent mixture and microfluidized with a lipid surfactant to produce the particles of the invention. The surfactant mixture is typically comprised of phosphatidylcholine, phosphatidylethanolamine with and without polyethylene glycol spacers for ligand coupling, and other lipid conjugates for targeting and fluorescent imaging. To further enhance the metal payloads provided by the amphiphilic gadolinium inverted micelles, organosoluable gadolinium may be incorporated into the oil matrix (for instance, pentanedione-gadolinium (III) may be used).

More specifically, hyperbranched, dendritic, or star polymers (for instance, polyethylenimine) are grafted with hydrophobic alkyl groups (e.g., 2-hexadecyloctadecanoic acid, 10,12-pentacosadiynoic acid, cholanic acid, linoleic acid or palmitic acid) by covalent means. The fatty acids are activated with 1-ethyl-3-(3-dimethyl amino propyl) carbodimide (EDAC) followed by addition of the hyper branched polymer to achieve greater than 50% functionalization of the free primary amine groups. For instance, in a typical experimental procedure, 10,12-pentacosadiynoic acid (0.5 g, 0.0013 moles, 0.6 equiv. of the 33% available free primary amine functionalities) is dissolved in 5 mL anhydrous chloroform (Aldrich chemicals). To this solution, is added a solution of 1-[3-(Dimethylamino)propyl]-3-ethylcarbodiimide methiodide (EDCl, Aldrich Chemicals, 0.5 g, 0.0017 moles, 1.3 equiv. of the carboxyl functionality) drop wise at room temperature over a 10 min period. The mixture is allowed to stir for 20 minutes at room temperature. The solution becomes colored, which confirms the formation of the activated carboxyl anions in the system. Polyethylenimine (branched, Mw=10 kDa, Alfa Aesar, 0.1 g, 60% target functionalization of the 33% available free primary amine functionalities) is added in 2 mL of anhydrous chloroform. The dark color of the solution turned pale after 2 h of stirring at room temperature. The mixture was stirred overnight at room temperature. The solvent was evaporated off under reduced pressure and the hydrophobically modified polymer was purified by repeated precipitation from diethyl ether. The polymer is typically stored at +4° C. and is stable for >6 months.

These hydrophobic polymers assume a 7-15 nm sized inverted micellar structure in organic solvent after vortexing. More specifically, the pentacosadiynoic acid grafted polyethylenimine is taken as a chloroform solution with a concentration range of ($10^{-6}$-$10^{-5}$M) and gently vortexed for about a minute. The hydrophobic chains immediately orient themselves towards the organic media and thereby form inverted micelles with a hydrophilic inner core. The inverted micelles assume typically 7-15 nm size and to avoid micelle clustering, the concentration of the polymer solution in organic solvent is monitored by observing the solution state particles size using a dynamic light scattering method.

Guest compounds (e.g. FITC, Methyl Orange, Gd3+-DTPA, nanometer sized gold colloids) are encapsulated within the inverted micelle by gentle inversion mixing (1:1 v/v). In a typical phase-transfer experiment, an aqueous solution of water soluble $Gd^{3+}$-DTPA solution (50 mg, 4 mL) is mixed with inverted micelle solution in anhydrous chloroform (5 mL) and inverted gently for few minutes. After standing and phase separation, the organic phase containing the polymeric inverted micelles is recovered, dried over a sodium sulfate column, and mixed with vegetable oil by vortexing (~1:1 v/v). In a typical experimental procedure, chloroform solution of gadolinium encapsulated inverted micelles is mixed with peanut oil by vortexing (~1:1 v/v). The organic solvent is evaporated from the oil using a standard rotary evaporation technique under reduced pressure. To increase the gadolinium payload, the vegetable oil may be pre-enriched with varying amounts of organo-soluble pentanedione-gadolinium (III) (0.1 gm, Aldrich) in chloroform prior to the microfludization. If desired, the pentanedione-gadolinium (III) can be used alone without the presence of the polymeric inverted micelles. The metal suspended oil is stable for months before sedimentation is observed. Furthermore, to increase the gadolinium payload, the vegetable oil may also be pre-enriched with varying amounts of hydrophobically modified gadolinium oxide nanoparticles in chloroform prior to the microfluidization. If desired, they can be used alone without the presence of the polymeric inverted micelles.

The final particle is produced by microfluidization of the gadolinium-polymer-oil mixture (20% v/v), an outer layer component co-mixture (2.0%, w/v), glycerin (1.7%, w/v), and water for the balance. The outer layer component co-mixture may include about 50 to about 70 mole % highly purified egg yolk lecithin (Avanti Polar Lipids, Inc), about 0 to about 1 mole % 1,2-dipalmitoyl-sn glycero-3-phosphoethanolamine-N-4-(p-maleimidophenyl)butyramide (MPB-PE, Avanti Polar Lipids) and/or amine-$PEG_{2000}$-phosphatidylethanolamine (amine-PE, Avanti Polar Lipids) for coupling, about 2 mole % phosphatidylethanolamine (PE), and about 0 to 20 mole % cholesterol. More specifically, in a typical experimental procedure, the outer layer component co-mixture may include 61 mole % highly purified egg yolk lecithin (Avanti Polar Lipids, Inc), 1 mole % biotinylated-phosphatidylethanolamine (BiotinPE), and 8 mole % cholesterol and 30 mole % gadolinium-DTPA-BOA. The surfactant components are dissolved in chloroform/methanol, evaporated under reduced pressure, dried in a 50° C. vacuum oven overnight and dispersed into water by sonication. The mixture is vigorously blended for few minutes and then continuously processed at 20,000 PSI for 4 minutes with an S110 Microfluidics fluidizer (Microfluidics). With the use of a laser lightscattering submicron particle size analyzer (Malvern Instruments), particle sizes are determined in triplicate at 37° C. to be nominally 270±20 nm and the electrophoretic light scattering experiment determines the potential value as ~–38 mV.

In some experiments, particles are modified to include a fluorescent lipid-conjugated marker, such as rhodamine (Avanti Polar Lipids, Inc.) or Alexafluor cyan dyes (Invitrogen) complexed with phosphatidylethanolamine. Nontargeted particles are prepared similarly except that the ligand-lipid conjugates are replaced with lecithin.

Figure 3:
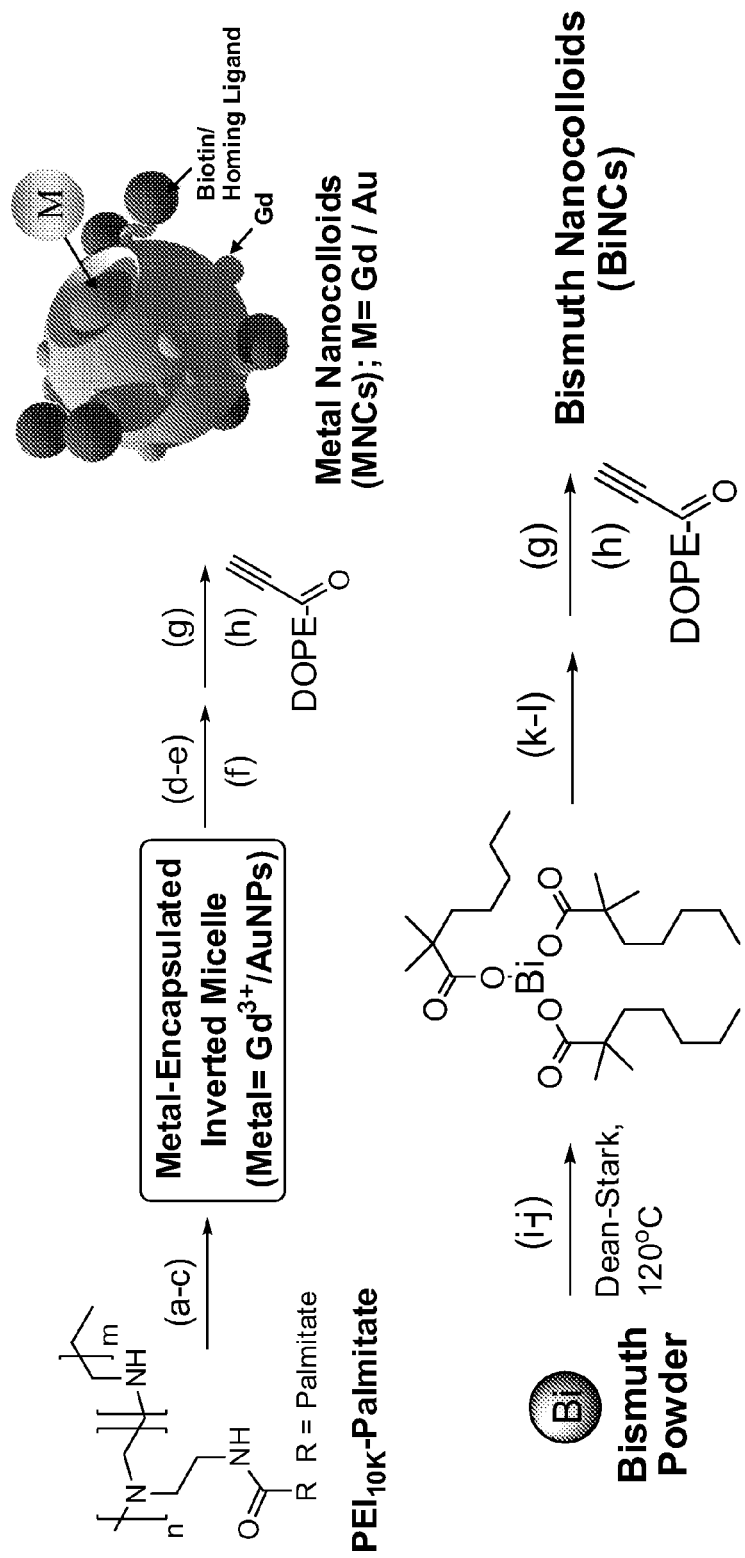
FIG. 3 depicts an illustration of the preparation of a particle of the invention comprising gadolinium, gold and bismuth. (a) reverse micelle formation; (b-c) inversion and encapsulation of water soluble Gd3+-DTPA or MesoGold® (2-3 nm); (d) suspended with vegetable oil; (e) organo soluble Gd-hexanedione or octane thiol capped AuNPs (5 nm); (f) phospholipids (optional use of DOPE-COCCH) formulation (g) coupling of anti-fibrin antibody/peptide; (h) Cu(I) catalyzed "Click Chemistry" cross-linking; (i) Oleic/Neodecanoic acid, hydrazine hydrate; a) three stages of purification; (k) suspended with polysorbates; (l) phospholipids (optional use of DOPE-COCCH); microfluidization.

See FIG. 3 for a schematic representation of the preparation of a metal encapsulated nanocolloid of the invention.

Characterization of the Gadolinium Based Particles

In process analyses for quality assurance include, $^1$H NMR, FT-IR and MALDI-MS spectrometry to measure and control the extent of hydrophobic-modification applied to the polymers. The phase transfer step is observed by UV-VIS and FT-IR with model chromophoric compounds to demonstrate the incorporation of water-soluble guests into the polymeric inverted micelles. To avoid micelle clustering, the concentration of the polymer solution in organic solvent is monitored by observing the solution state particles size using a dynamic light scattering method.

The final lipid-encapsulated particle is characterized for size and surface potential with a Brookhaven Zeta Plus or Malvern Zetasizer lightscattering particle analyzer with typical values ranging from 190 to 250 nm with polydispersities around 0.12-0.2. Zeta potential values range between –20 and –50 mV. Total gadolinium content is determined by ICP-MS (Bodycote, Calif.) or neutron activation analysis (MURR, University of Missouri, Columbia, Mo.). Particle number is estimated from the nominal particle volume and the volume of the oil-polyethylenimine-Gd-DTPA mixture. Targeting agent concentration (F(ab) or peptide) is estimated from the uncoupled ligand concentration in the excipient before dialysis determined by HPLC subtracted from the total amount of compound applied, and the difference divided by the number of particles per ml. All analytical methods are conducted in triplicate.

Example 2

Synthesis and Characterization of Bismuth Particles

Following a strategy similar to that detailed in example 2, a prototype particle with a nominal hydrodynamic diameter between 200-350 nm with a payload of 500,000 to 1,000,000 bismuth metal atoms per bound particle has been prepared. (See FIG. 1) These particles incorporate bismuth organometallic chelates (e.g. bismuth neodecanoate) which are suspended in sorbitan sesquioleate and microfluidized with a lipid surfactant to produce particles of the invention. The surfactant mixture is typically comprised of phosphatidylcholine, phosphatidylethanolamine with and without polyethylene glycol spacers for ligand coupling, and other lipid conjugates for targeting and fluorescent imaging.

The final particle is produced by microfluidization of the bismuth neodecanoate-oil mixture (20% v/v), a outer layer component co-mixture (2.0%, w/v), glycerin (1.7%, w/v), and water for the balance. The outer layer component co-mixture may include about 50 to 70 mole % highly purified egg yolk lecithin (Avanti Polar Lipids, Inc), about 0 to 1 mole % 1,2-dipalmitoyl-sn glycerol-3-phosphoethanolamine-N-4-(p-maleimidophenyl)butyramide (MPB-PE, Avanti Polar Lipids) and/or amine-$PEG_{2000}$-phosphatidylethanolamine (amine-PE, Avanti Polar Lipids) for coupling, about 2 mole % phosphatidylethanolamine (PE), and about 0 to 20 mole % cholesterol. For instance, in a typical experimental procedure, the outer layer component co-mixture includes 90 mole % highly purified egg yolk lecithin (Avanti Polar Lipids, Inc), 1 mole % biotinylated-phosphatidylethanolamine (BiotinPE), and 9 mole % cholesterol. The surfactant components are dissolved in chloroform/methanol, evaporated under reduced pressure, dried in a 50° C. vacuum oven overnight and dispersed into water by sonication. The mixture is vigorously blended for few minutes and then continuously processed at 20,000 PSI for 4 minutes with an S110 Microfluidics fluidizer (Microfluidics). With the use of a laser lightscattering submicron particle size analyzer (Malvern Instruments), particle sizes are determined in triplicate at 37° C. to be nominally 270±20 nm and the electrophoretic light scattering experiment determines the zeta potential value as ~−20 mV.

Example 3

Synthesis and Characterization of Gold Particles

Following a strategy similar to that detailed in example 3, a prototype particle with a nominal hydrodynamic diameter between 200-250 nm with a payload of 500,000 to 1000,000 gold metal atoms per bound particle has been prepared. (See FIG. 1) These particles incorporate gold organometallic chelates (e.g. gold 2-ethylhexanoate) which are suspended in sorbitan sesquioleate and microfluidized with a lipid surfactant to produce particles of the invention. The surfactant mixture is typically comprised of phosphatidylcholine, phosphatidylethanolamine with and without polyethylene glycol spacers for ligand coupling, and other lipid conjugates for targeting and fluorescent imaging.

The final particle is produced by microfluidization of the bismuth neodecanoate-oil mixture (20% v/v), a outer layer component co-mixture (2.0%, w/v), glycerin (1.7%, w/v), and water for the balance. The outer layer component co-mixture may include about 50 to 70 mole % highly purified egg yolk lecithin (Avanti Polar Lipids, Inc), about 0 to 1 mole % 1,2-dipalmitoyl-sn glycerol-3-phosphoethanolamine-N-4-(p-maleimidophenyl)butyramide (MPB-PE, Avanti Polar Lipids) and/or amine-$PEG_{2000}$-phosphatidylethanolamine (amine-PE, Avanti Polar Lipids) for coupling, about 2 mole % phosphatidylethanolamine (PE), and about 0 to 20 mole % cholesterol. For instance, in a typical experimental procedure, the outer layer component co-mixture includes 90 mole % highly purified egg yolk lecithin (Avanti Polar Lipids, Inc), 1 mole % biotinylated-phosphatidylethanolamine (BiotinPE), and 9 mole % cholesterol. The surfactant components are dissolved in chloroform/methanol, evaporated under reduced pressure, dried in a 50° C. vacuum oven overnight and dispersed into water by sonication. The mixture is vigorously blended for few minutes and then continuously processed at 20,000 PSI for 4 minutes with an S110 Microfluidics fluidizer (Microfluidics). With the use of a laser lightscattering submicron particle size analyzer (Malvern Instruments), particle sizes are determined in triplicate at 37° C. to be nominally 270±20 nm and the electrophoretic light scattering experiment determines the zeta potential value as ~−20 mV.

In some experiments nanoparticles are modified to include a fluorescent lipidconjugated marker, such as rhodamine (Avanti Polar Lipids, Inc.) or Alexafluor cyan dyes (Invitrogen) complexed with phosphatidylethanolamine. Nontargeted particles are prepared similarly except that the ligandlipid conjugates are replaced with lecithin.

Particles may be characterized analogously to the particles in Example 1.

Following a strategy similar to that detailed in Example 2, biotinylated bismuth nanocolloids (BiNC) were also prepared by suspending bismuth neodecanoate (Aldrich Chemicals, Inc.) in sorbitan sesquioleate (Aldrich Chemicals, Inc.), and vigorously vortexed to homogeneity. The bismuth neodecanoate-sorbitan sesquioleate mixture (20% v/v), was combined with a surfactant co-mixture (2.0%, w/v), glycerin (1.7%, w/v), and water (77.3% w/v). The surfactant co-mixture included high purity egg yolk phosphatidylcholine (90 mole %, Avanti Polar Lipids, Inc.), cholesterol (8 mole %, Aldrich Chemicals, Inc), biotinylated-dipalmitoyl phosphatidylethanolamine (2 mole %, Avanti Polar Lipids, Inc.). Control nanocolloids were prepared following identical procedure except the metal was omitted. The nanoparticles were dialyzed against water using a 10,000 Da MWCO cellulose membrane then passed through a 0.45 μm Acrodisc Syringe filter. Bismuth nanocolloid nominal particle size was 210±9 nm; polydispersity and zeta potential were 0.17±0.02 and −22±7 mV (Brookhaven Instrument Co.) respectively. Bismuth content, determined by ICP OES, was nominally 200 μg/ml of the 20% colloid suspension.

The spectral CT prototype scanner and data processing method has been previously reported 18, 25 for imaging phantoms. Optimized parameters for the detection of bismuth with K-edge energy of 90.8 keV were determined by simulation: tube voltage was set to 130~kVp and the six tunable energy-thresholds were 25.0, 48.0, 55.0, 85.0, 91.0, 110.0 keV on all 1024 pixels of the CdTe detector array. The scanner was operated at high magnification; images were reconstructed on an isotropic grid of 100×100×100 mm3. Clot phantoms were scanned at 10 mAs per slice; the human carotid samples at 7.5 mAs per slice. The attenuation was decomposed into photo-effect, Compton-effect and bismuth.

Clot phantoms were prepared from fresh, sodium citrate anticoagulated blood (9:1, vol/vol) by combining plasma and 100 mmol/L calcium chloride (3:1 vol/vol) with 5 U thrombin (Sigma-Aldrich, Inc.) in a plastic tube mold through which a 5-0 suture was passed to provide a suspension. The plasma coagulated at room temperature. The clots were removed from the mold and then were incubated individually with 150 μg biotinylated antifibrin monoclonal antibody (NIB 1H10) in 10 mL PBS with 1% crystalline BSA (Sigma Chemical Co) for 2 hours at 37° C. The washed, antibody-treated clots were then incubated with excess avidin (50 μg/mL PBS) for 30 minutes, washed, followed by biotinylated bismuth nanocolloids (30 μL/mL PBS) for 30 minutes and washed again. The control clots were treated similarly with control nanocolloids (30 mL/mL PBS).

Spectral CT bismuth concentration data were analyzed using ANOVA procedure provided by SAS (SAS, Inc, Cary, N.C.) using a $p<0.05$ statistical threshold of significance.

Figure 4A:
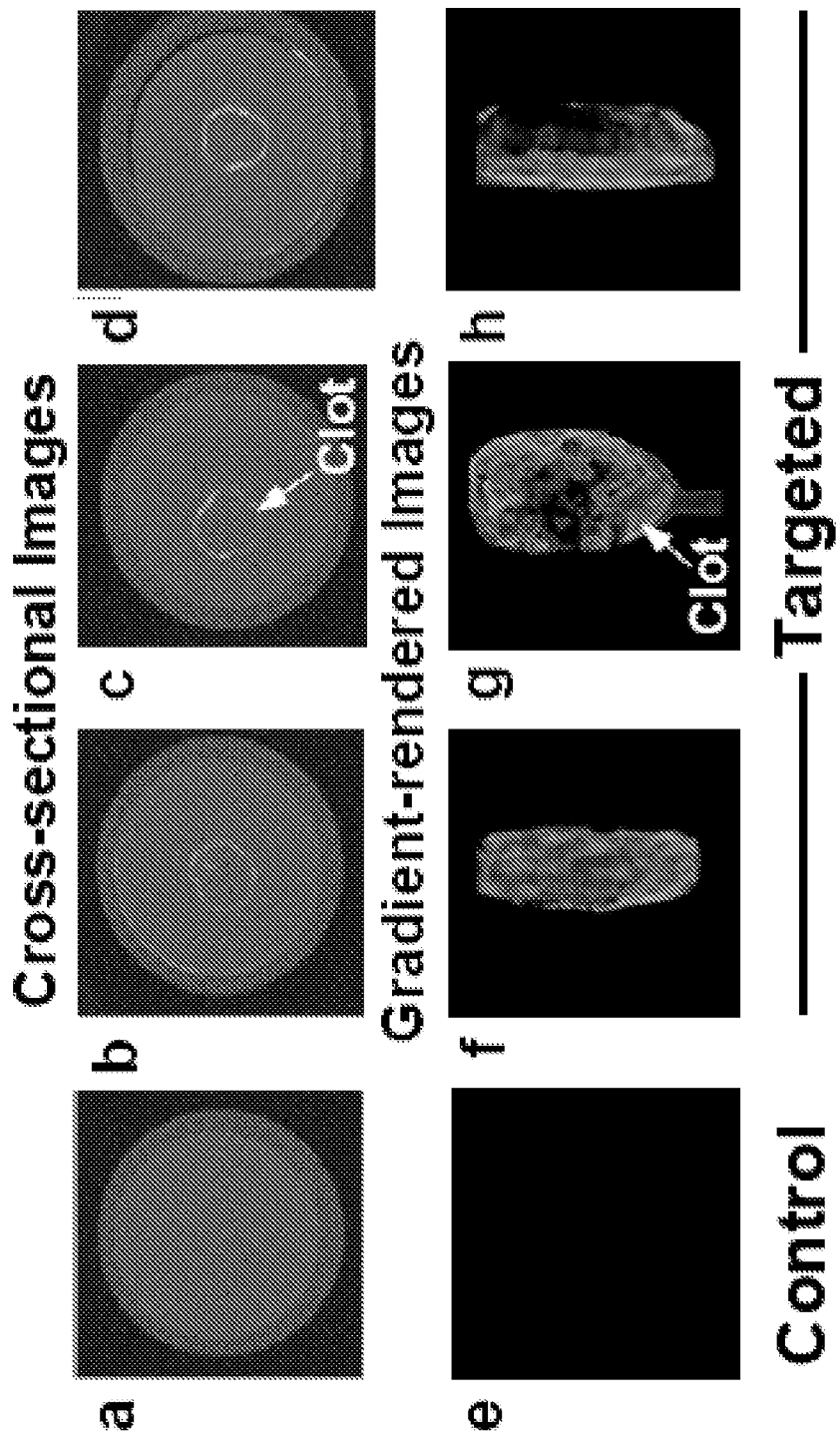
FIG. 4 (A) depicts spectral CT cross-sectional slices (Top) and gradient rendered images (Below) of fibrin clots targeted with control (a, e) and bismuth nanocolloids (BiNC) replicates (b-d, f-h); (Scale: 10 mm). (B) Integral bismuth distribution in axial slices of fibrin clots: bound on bismuth layer thickness calculated with Scanner spatial resolution @100 mm, Voxel size in reconstructed image: (100 mm)3, bismuth layer thickness: 1-2 voxel; Bismuth surface density was calculated from integrations perpendicular to the surface layer corresponding to an average 3.5 mass % bismuth for a 100 mm layer thickness.
Figure 4B:
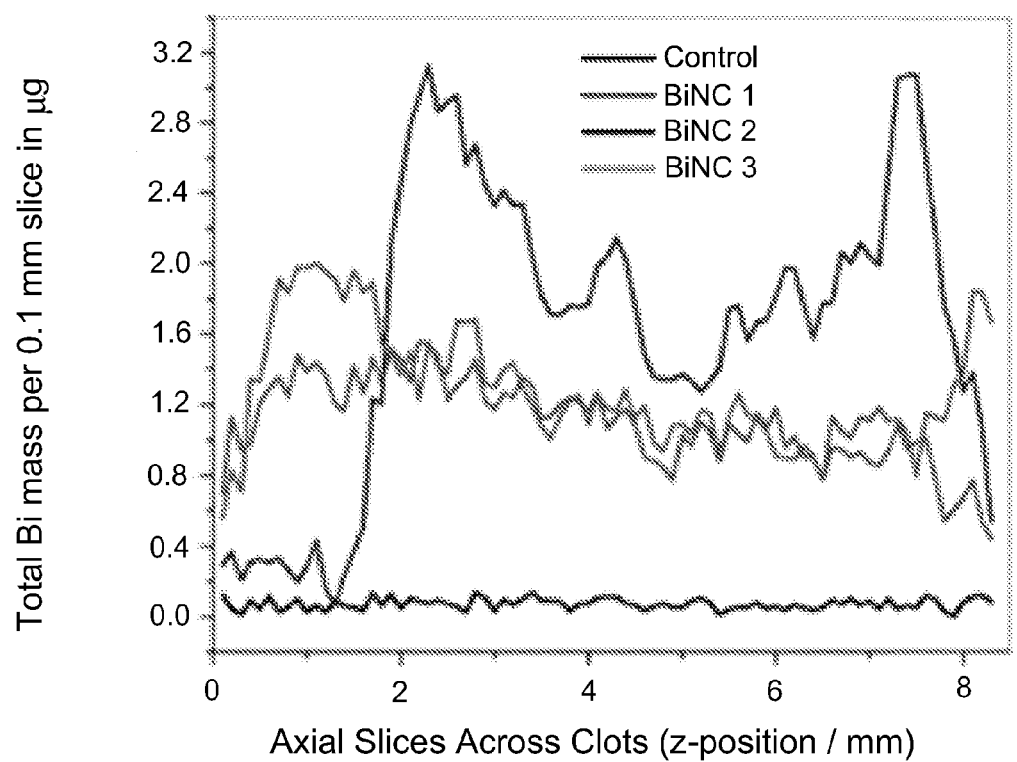

Fibrin-rich clots supported on silk suture were suspended in phosphate buffered saline (PBS, pH 7.4) within sealed polystyrene test tubes (75 mm). Biotinylated bismuth nanocolloid (BiNC) and the control nanocolloid (i.e., containing no metal) were targeted to the fibrin clots with classic avidin-biotin interactions using a well-characterized biotinylated fibrin-specific monoclonal antibody (NIB5F3). The first Spectral CT images of targeted fibrin clot samples in cross-section (top row) and their following 3D maximum intensity projection reconstructions (bottom row) are presented in FIG. 4. The control (top far left) clot treated with targeted nonmetallic nanoparticles had negligible contrast, whereas, the binding of BiNC provided excellent delineation and signal enhancement of the clot surface. The nominal size of the nanoparticles (250 nm) precluded deep penetration through the tight weave of fibrin fibrils.

Bismuth layer bound on the surface of the clots was 1 to 2 voxels (100 μm×100 μm×100 μm) thick and the average density in the surface layer was found to be 3.5 mass % of bismuth for a layer thickness of 100 μm. The total bismuth mass per clot was calculated to be 91±0.3, 136±0.8 and 107±0.3 mg, respectively, for the three independent syntheses of BiNC versus the control 0. Detailed BiNC concentration data on a per slice basis may be found in FIG. 4C.

Example 4

Targeting Bismuth Particles to Fibrin in a Physiological Sample

Figure 5:
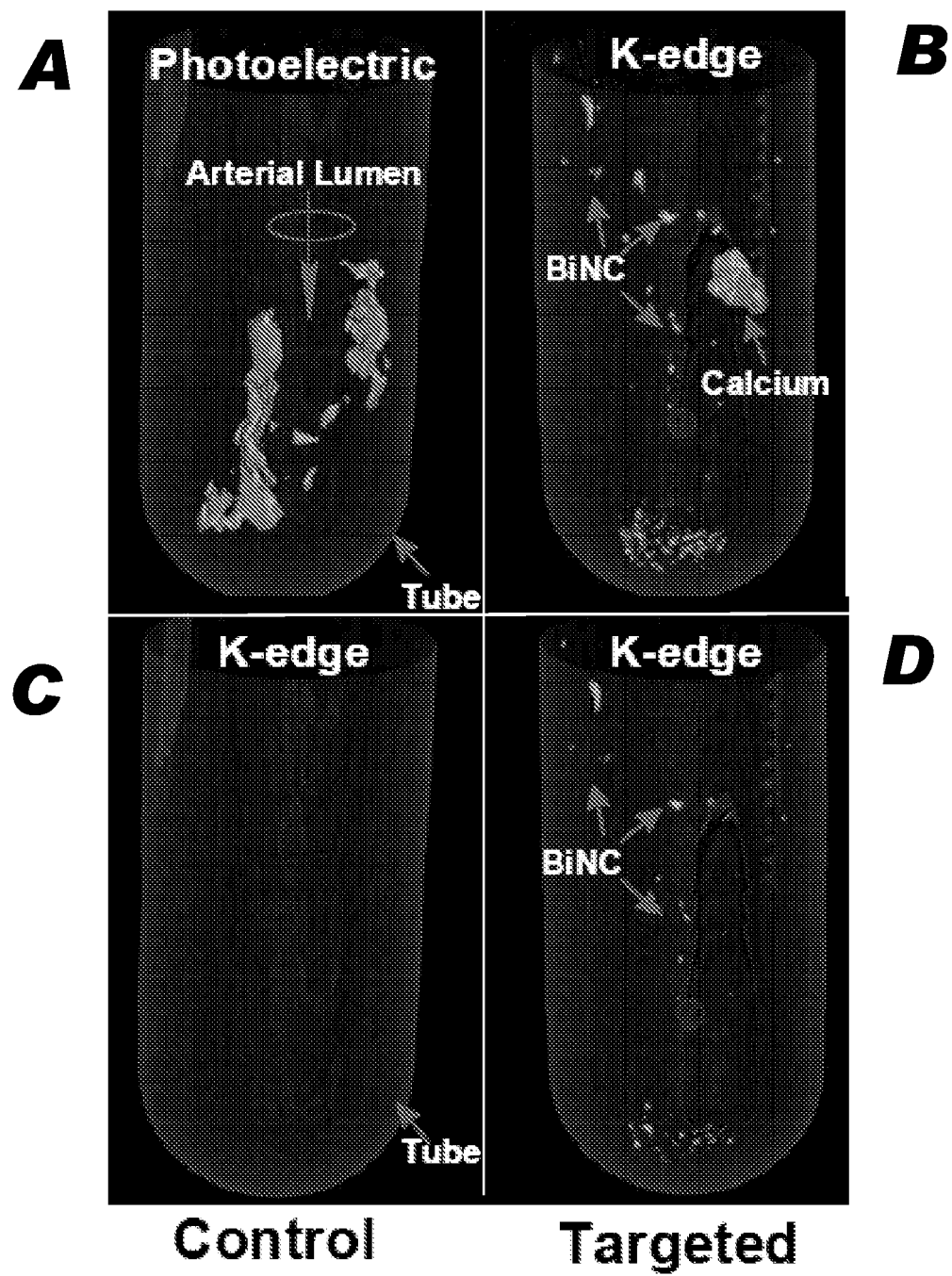
FIG. 5 depicts the lowest energy bin images with bismuth overlay (a) and (b) and bismuth basis Spectral CT images (c) and (d) of human carotid specimen incubated with control nanocolloids and bismuth nanocolloids (BiNC) respectively; Note the complete absence of Bi in the control sample (a) and (c).

For a physiological example of fibrin targeting using BiNC particles described in Example 3, human carotid artery endarterectomy (CEA) specimens from symptomatic patients were utilized.
Human Carotid Samples Human carotid endarterectomy samples were obtained post-surgically from symptomatic patients and frozen until treatment. After being thawed, the carotid artery was rinsed with sterile saline to remove residual blood. The artery was incubated with 125 mg biotinylated anti-fibrin monoclonal antibody (NIB 1H10) overnight at 4° C., followed by 125 mg avidin for 1 hr at 37° C., and then 100 mL of the selected biotinylated nanoparticles for 1 hr at 37° C. to complete the binding. All samples were rinsed three times with sterile saline after each incubation step to remove any unbound reactants. Following the last incubation step, the carotid specimens were immersed in agarose for shipment and imaging.
Results The experimental results of CEA specimens targeted with fibrin-specific BiNC or control nanocolloids and imaged with Spectral CT are presented in FIG. 5. The enhanced attenuation of the small fibrin deposits in the ruptured carotid plaque treated with targeted metal colloid (90.8 keV) was easily appreciated and resolved from the abundant x-ray attenuation due to plaque calcium (4.0 keV) (panels "b", "d"). In contradistinction, only the calcium deposits are detected in the control (panels "a", "c"). As is typical of CT at these energies, the calcium and bismuth signatures were seen, but the poorly attenuating soft-tissue detail was lost. Positive diagnosis of nascent thrombus in the coronaries of patients presenting to the emergency room with recent chest pain could resolve the need for coronary catheterization directly and avoid current costs and risks associated with hospitalization and further screening (e.g., stress testing).

Example 5

Microscopic Analysis of Fibrin Targeting Bismuth Particles

Figure 6:
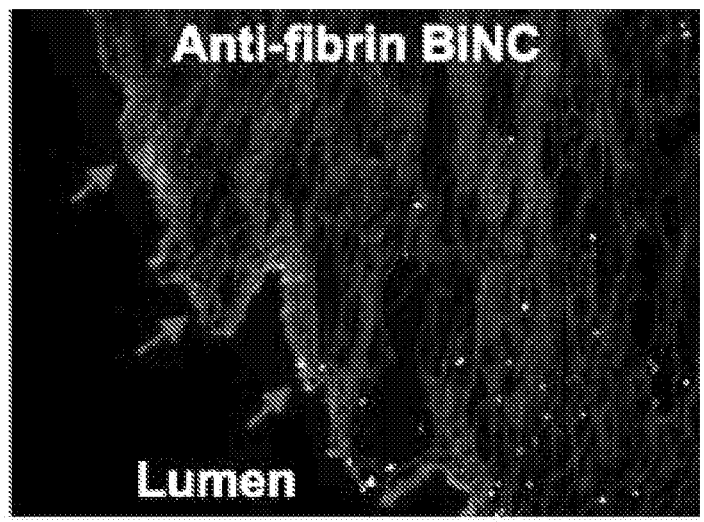
FIG. 6 depicts frozen sections of CEA specimens exposed to rhodamine-labeled BiNC with (A) or without (C) fibrin-antibody targeting and counterstained with DAPI nuclear staining (blue) (B and D). Immunostaining of adjacent sections demonstrate the presence of fibrin on the lumen surface, corresponding to BiNC rhodamine signal, and within the plaque, where BiNC nanoparticles were unable to penetrate.
Figure 6:
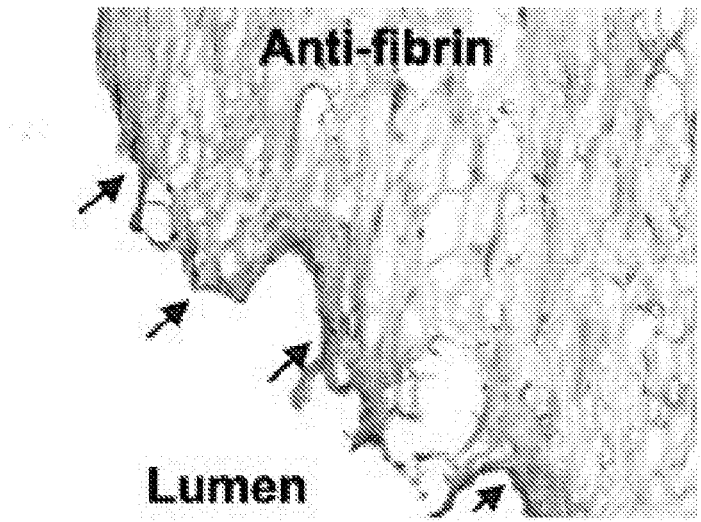
Figure 6:
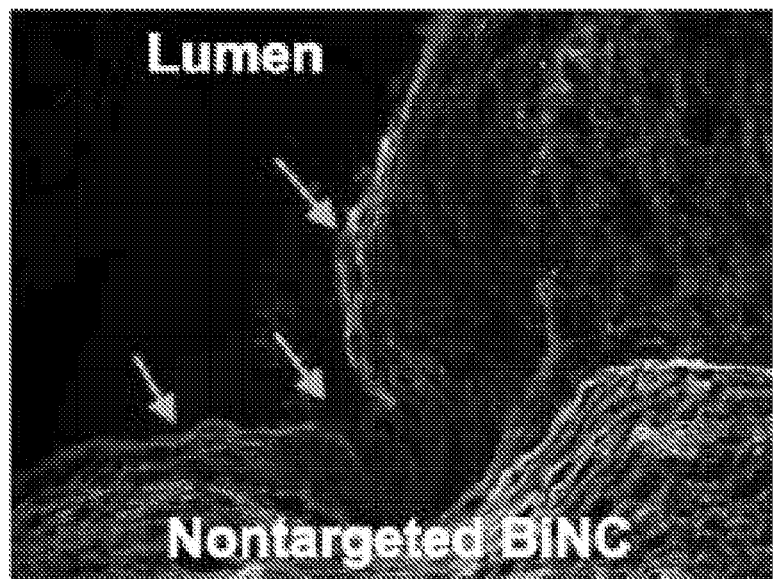
Figure 6:
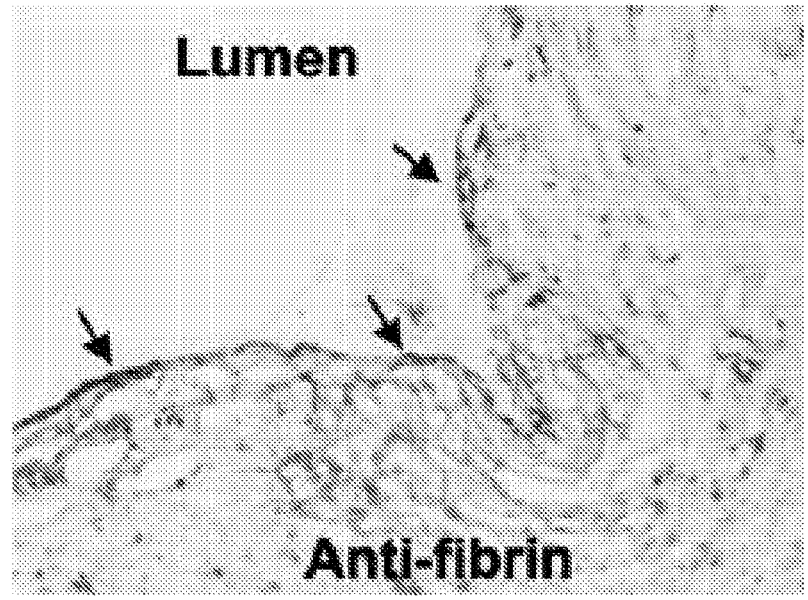

The specific targeting of BiNC particles described in Example 3 to fibrin presented on human carotid endarterectomy specimens was studied microscopically.
Histology Human carotid endarterectomy specimens were thawed then serially incubated with anti-fibrin monoclonal antibody (NIB 1H10), avidin, and biotinylated rhodamine BiNC. Control CEAs were treated identically except the anti-fibrin antibody was excluded. Unbound reactants were removed between each step. The tissues were embedded in O.C.T. media (Fisher Scientific), cryosectioned (8 μm), and adjacent sections were either counterstained with DAPI for fluorescent microscopy or immunostained with anti-fibrin antibody (1H10) using routine technique and the Vectastain ABC kit (Vector Laboratories, Burlingame, Calif.). Microscopic imaging was performed with Olympus BX61 using a Color View II camera for light microscopy, F-View II B&W CCD camera for fluorescent images, MicroSuite biological suite software for microscope control and image processing (Olympus America, Inc., Center Valley, Pa.).
Results Frozen sections of CEA specimens exposed to rhodamine-labeled BiNC (FIG. 6) with (panel "a") or without (panel "c") fibrin-antibody targeting and counterstained with DAPI nuclear staining (blue) illustrate the ligand-specific binding of the red BiNC to fibrin layered along the luminal aspect of the CEA tissue (FIG. 6). Nontargeted BiNC did not adhere to the control carotid specimen. Immunostaining of adjacent sections demonstrated the presence of fibrin on the lumen surface, corresponding to BiNC rhodamine signal, and also within the plaque, where BiNC nanoparticles were unable to penetrate. These results demonstrate that the Spectral CT signal derived from fibrin-bound BiNC reflects high-risk intraluminal thrombus and not other prevalent extraluminal sources of fibrin, such as intraplaque hemorrhage.

Example 6

Synthesis and Characterization of Targeted Bismuth Particles

Figure 7:
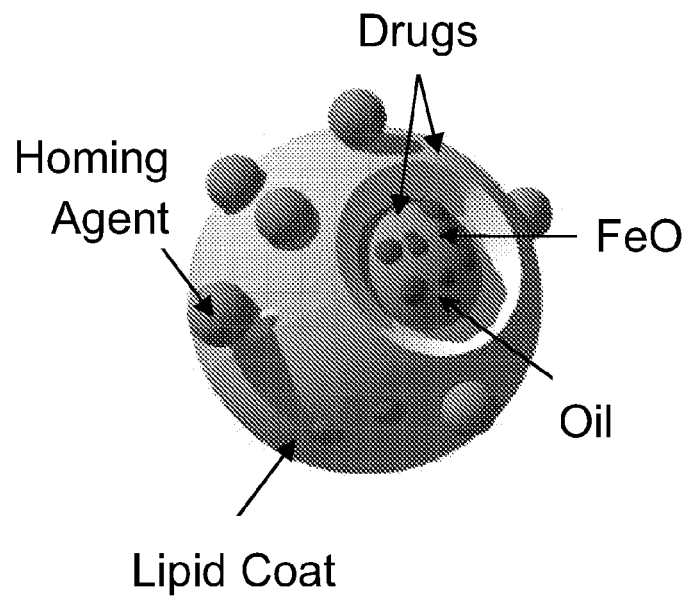
FIG. 7 is a schematic of a lipid-encapsulated magnetic oxide particle.

"Soft" metal nanocolloid K-edge agents, which can be homed to a target within intravascular thrombus were developed (FIG. 7, unmarked figure). These particles provide the location and concentration of targeted K-edge material, which can be overlaid onto the traditional anatomical images of multislice CT. To demonstrate the concept, in vitro protocols were utilized to evaluate Spectral CT contrast agents thus targeted.

Example 7

Figure 2:
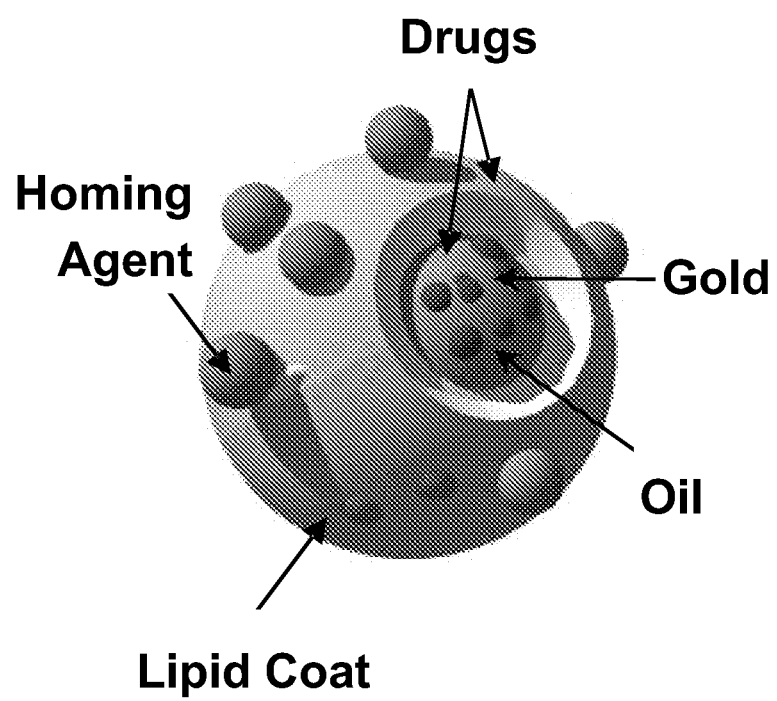
FIG. 2 depicts an illustration of a particle with a nominal diameter of 160 nm and an inner core comprising gold nanoparticles. The particle has a zeta value of ~−30 mV.

Synthesis and Characterization of Gold Nanocolloids from Water-Soluble Gold Nanoparticles The unique phase transition of the water soluble guests through the inverted micellar container has been further exploited to prepare gold encapsulated particles of the invention. A prototype particle with a nominal hydrodynamic diameter between 180-250 nm with a payload of 100,000-500,000 gold (AuNPs) nanoparticles per bound particle has been prepared. (See FIG. 2) These nanoparticles incorporate an amphiphilic polymer that is complexed non-covalently to MesoGold® (Pure Colloids, Inc., ~3-4 nm sized colloidal aqueous suspension of gold nanoparticles) to form gold-encapsulated inverted micelles. These inverted micelles are suspended in oil and microfludized with a lipid surfactant to produce particles of the invention. To increase the gold payload, the vegetable oil maybe pre-enriched with varying amounts of hydrophobically coated gold nanoparticles in toluene prior to the microfluidization. The surfactant mixture is typically comprised of phosphatidylcholine, phosphatidylethanolamine with and without polyethylene glycol spacers for ligand coupling, and other lipid conjugates for targeting and fluorescent imaging.

More specifically, hyperbranched or dendritic polymers are grafted with hydrophobic alkyl groups (e.g., 10,12-pentacosadiynoic acid, hexadecyloctadecanoic acid, cholanic acid, linoleic acid etc.) by covalent means. The fatty acids are activated with EDAC followed by addition of the polymer to achieve greater than 50% functionalization of the free primary amine groups. These hydrophobic polymers assume a 10-15 nm sized inverted micellar structure in organic solvent after vortexing.

A colloidal aqueous suspension of gold nanoparticles is encapsulated within the inverted micelle by gentle inversion mixing (1:1 v/v). In a typical phase-transfer experiment, a solution of Mesogold® (Purecolloids, Inc., 3-4 nm colloidal gold particles (5×4 mL)) is mixed with the inverted micelle solution in anhydrous chloroform (5 mL) and inverted gently for few minutes. The transport of gold nanoparticles from water to organic phase is visually observed. The organic phase containing the polymeric inverted micelles is recovered, dried over a sodium sulfate column, and mixed with oil by vortexing (~1:1 v/v). In a typical experimental procedure, a chloroform solution of Mesogold® encapsulated within inverted micelles is mixed with oil (for instance, peanut oil; 4.5 mL) by vortexing (~1:1 v/v). The organic solvent is evaporated from the oil using a standard rotary evaporation technique under reduced pressure. The metal suspended oil is stable for months before sedimentation is observed.

To increase the gold payload, the oil may be pre-enriched with varying amounts of octanethiol coated gold nanoparticles (Sigma-Aldrich, 2-4 nm particle size, 2% (w/v) in toluene) prior to the microfludization. The organosoluble gold particles may also be generated in the laboratory by following a literature procedure (Lala et. al. Langmuir, 17 (12), 3766 3768, 2001). Briefly, gold particles are synthesized in water and capped with octadecanethiol molecules to render them water soluble through complexing with α-cyclodextrin molecules. The water soluble gold nanoparticles are then transferred into chloroform by vortexing of a biphasic mixture of the α-CD-capped-ODT-stabilized gold particles and chloroform.

The final particle is produced by microfluidization of the gold nanoparticle-polymer-oil mixture (20% v/v), outer layer component co-mixture (2.0%, w/v), glycerin (1.7%, w/v), and water for the balance. The outer layer component co-mixture includes about 50 to 70 mole % highly purified egg yolk lecithin (Avanti Polar Lipids, Inc), about 0 to 1 mole % 1,2-dipalmitoyl-sn glycerol-3-phosphoethanolamine-N-4-(p-maleimidophenyl)butyramide (MPB-PE, Avanti Polar Lipids) and/or amine-$PEG_{2000}$-phosphatidylethanolamine (amine-PE, Avanti Polar Lipids) for coupling, about 2 mole % phosphatidylethanolamine (PE), and about 0 to 20 mole % cholesterol. For instance, in a typical experimental procedure, the outer layer component co-mixture includes 89 mole % highly purified egg yolk lecithin (Avanti Polar Lipids, Inc), 1 mole % biotinylated-phosphatidylethanolamine (BiotinPE), and 10 mole % cholesterol. The surfactant components are dissolved in chloroform/methanol, evaporated under reduced pressure, dried in a 50° C. vacuum oven overnight and dispersed into water by sonication. The mixture is vigorously blended for few minutes and then continuously processed at 20,000 PSI for 4 minutes with an S110 Microfluidics fluidizer (Microfluidics). With the use of a laser lightscattering submicron particle size analyzer (Malvern Instruments), particle sizes are determined in triplicate at 37° C. to be nominally 170 nm and the electrophoretic light scattering experiment determines the zeta potential value as ~−30 mV.

In some experiments nanoparticles are modified to include a fluorescent lipidconjugated marker, such as rhodamine (Avanti Polar Lipids, Inc.) or Alexafluor cyan dyes (Invitrogen) complexed with phosphatidylethanolamine. Nontargeted particles are prepared similarly except that the ligand-lipid conjugates are replaced with lecithin.

Particles may be characterized analogously to the particles in Example 1.

Example 8

Demonstrate and Optimize Fibrin-Bound Particles for Spectral CT Contrast Using Clot Phantoms The particles developed above are evaluated for contrast detectability in vitro using fibrin clot phantoms to which the particles are targeted to the surface through biotin-avidin interactions. After acceptable Spectral CT contrast has been demonstrated, the best versions are coupled with either anti fibrin f(ab) fragments or fibrin binding peptide, including the published peptide backbone of the EPIX fibrin-specific paramagnetic chelate (Wescott C R et al PCT WO 01/09188 A1, 2001). The surface concentration of the anti-fibrin ligands will be varied and the dissociation characteristics of the ligand conjugated particles will be determined as described below.

Assessment of Spectral CT Contrast

Initial assessments of the particles are performed on serial dilutions spanning an empiric concentration range between 1 µM and 100 µM of particles. Plastic ampules of particles will be prepared, imaged, and quantified with Spectral CT as previously shown for gadolinium DTPA in Example 1. Each type of particle will be submitted for quantitative metal analysis using ICP-MS or neutron activation. Based on an expected low variability within samples and a two decade dilution range, we anticipate that 4 replicates of each particle-concentration combination will permit a 20% difference in contrast to be detectable with 80% power at an alpha level of 0.05. Slopes of the regression of signal change versus particle concentration will be calculated and compared using general linear models (SAS, Inc., Cary, N.C.).

Next, acellular fibrin clot phantoms are produced from citrated human plasma combined with 500 mM calcium chloride and thrombin (3 U/µL). Each clot is formed by quickly dispensing this mixture (400 µL) onto a nitrocellulose membrane substrate and by allowing the mixture to coagulate for 2 minutes. The clot samples are then immersed in phosphate buffered saline (PBS). The clots are treated serially with excess biotinylated anti-fibrin antibody, washed in PBS, exposed to excess avidin, washed in PBS, and then incubated with either a biotin-targeted version of the particles, a non-gadolinium analogue of the biotinylated particles, or a non-targeted version of the particles. The fibrin clots are washed before imaging to minimize nonspecific adherence of particles. Spectral CT images and photon quantification will be performed at different voxel sizes and x-ray power.

To characterize the sensitivity of detection of preferred particles further, acellular clot phantoms are treated sequentially with biotinylated antifibrin antibody and avidin as above but are exposed to varying ratios of biotinylated particles with and without incorporated gadolinium: 1:0, 1:1, 1:10, 1:100, respectively. Based on a minimum of 30% change in clot contrast with a coefficient of variation for the method of 20%, it is anticipated that 8 replicates/treatment will provide 80% power at an alpha level of 0.05. Prior experience suggests that much greater changes with far less variability are likely.

Anti-Fibrin Targeting Molecules

Anti-fibrin monoclonal antibody (NIB 1H10, NIB 5F3)[18, 37] are produced and purified from hybridomas by conventional methods. Anti-fibrin F(ab) fragments are generated and isolated using an immunopure F(ab) preparation kit (Pierce, Rockford, Ill.). Briefly, IgG is dialyzed into 20 mM phosphate/10 mM EDTA buffer (pH 7.0), concentrated to 20 mg/ml and digested by immobilized papain. Solubilized F(ab)' is purified from Fc fragments and undigested IgG protein using a protein A column. F(ab) fragments are purified from excess cysteine using a G25-150 column and deoxygenated phosphate buffer (pH 6.7). Fraction identity is confirmed by routine SDS-PAGE procedures. An analogous nanocolloid using a nonspecific, porcine IgG (Sigma, Mo.) is used to prepare control ligands with random specificities. F(ab) fractions are pooled and combined with the MPB-PE derivatized nanocolloid (1-2 mg F(ab)/ml of nanocolloid). The mixture is adjusted to pH 6.7, sealed under nitrogen and allowed to react overnight at ambient temperatures with gentle, continuous mixing. The mixture is subsequently dialyzed with a 300,000 MWCO Spectra/Por DispoDialyzer (Laguna Hills, Calif.) against 10 mM phosphate buffer (pH 7.2) to remove unconjugated F(ab) fragments. The final nanocolloid is vialed under nitrogen and stored at 4° C. until use. A nonspecific control nanocolloid may be prepared using the control irrelevant IgG F(ab) fragments in the above protocol.

An ELISA assay to assess the bioactivity of the anti-fibrin IgG and its F(ab) fragments demonstrates the bioactivity of the intact anti-fibrin IgG surrogate, and the cut F(ab) fragments pre- and post-lyophilization as a function of different fibrinogen substrates. Additionally, coupling integrity of the lyophilized F(ab) was maintained using 50 or 250 mM trehalose as a cryoprotective and bulking agent. Using a polyethylene glycol 2000 tether, we have established that approximately 25 F(ab) or IgG ligands are optimally coupled per nanoparticle (250 nm) with relatively high efficiency (>80%), creating a highly multivalent targeting system. Using small peptides or mimetics and amide bond linkages, the conjugation efficiency is conservatively greater than 90% and the number of ligands per particle is approximately 10 fold greater.

In addition to the anti-fibrin antibodies, a peptide will be studied as potential homing ligand: EPIX-9. EPIX-9 (PCT WO 01/09188 A) is a family of fibrin-specific peptides discovered with phage display technology (DYAX, Inc.), which has 2.6 µm Kd and 190 µm Kd for human fibrin and fibrinogen, respectively. Lysine is added as the first amino acid with an orthogonal protecting group 4,4-dimethyl-2,6-dioxocyclohex-1-ylidene (ivDde) on the side chain. After chain elongation using standard Fmoc solid-phase peptide synthesis (SPPS) methodology, selective deprotection of the ivDde group is achieved by treatment with 2% hydrazine in DMF. Conjugation group 6-Boc-HNA (6-Boc-hydrazinonicotinic Acid) is added in the presence of HBTU (2-1H-benzotriazole-1-yl)-1,1,3,3-tetramethylaminium hexafluorophosphate), DIPEA and DMF, followed by simultaneous deprotection of the cysteines and disulfide bond formation is performed to cyclize the peptide. The peptide is cleaved from the resin and the remaining side-chain protecting groups are removed by treatment with trifluoracetic acid (TFA), $H_2O$, and triisopropylsilane (TIS). The final peptide is purified with HPLC, characterized with MS, and lyophilized in trehalose until use. Subsequent coupling to the particle will be analogous to the anti-fibrin F(ab) procedure described above.

Dissociation Constants with Respect to Fibrin

Particles covalently modified with targeting molecules at varying densities will be characterized for fibrin binding. A fibrinogen solution (10 mg/ml at 2-fold the concentration of fibrin expected) in TBS (50 mM Tris, 150 mM NaCl, pH 7.4) containing ~15 mM citrate will be prepared along with a second solution of thrombin (2 U/ml), 20 mM $CaCl_2$, and 5 mM ε-amino caproic acid in TBS. The fibrinogen and thrombin solutions will be mixed 1:1 (100 µl total) in the wells of a 96 well plate. Plates are dried overnight. The peptide or particle conjugate is added in 24 concentrations between 1 and 200 µM, the later on a particle basis, covered and incubated at 37° C. for 2 hours. The supernatant in each well is pipeted and the concentration of peptide is measured by HPLC/ELSD and the particles by metal content; both are compared to known standards. The concentration of the bound peptide or particle is determined by subtracting the concentration of free peptide or particle from the initial concentrations. Plotting bound vs. free peptide or particle provides an estimate of Kd and the concentration of bound peptide at saturation. The curve is fit to the equation [bound]=N×[Free]/Kd+[Free]. N is the concentration of binding sites and Kd is the dissociation constant, the reciprocal of Ka. The number of binding sites per fibrin molecule is estimated as N divided by the concentration of fibrin in the assay, typically 15 µM.

Since fibrinogen is a potential competitor to fibrin-targeting, measurements of binding affinity in the presence of physiological concentrations of fibrinogen will be evaluated as well. Free fibrinogen at various concentrations up to 400 mg/dl will be added in the presence of PPACK (D-phe-pro-arg-chloromethylketone) to abolish thrombin activity. Free and bound peptide or particles and the apparent Kd will be measured and determined as described above. All experiments are to be performed in triplicate and the average will be presented along with the standard error of the mean.

REFERENCES FOR EXAMPLES 1-8

1. Proska R, Grass M. Energy resolved photon counting for CT. WO2006117720 (2006).
2. Proska R. Quantitative material decomposition for spectral CT. WO2007034359 (2007).
3. Benson R. Present status of coronary artery disease. Arch Pathol Lab Med 1926; 2:876-916.
4. Constantinides P. Plaque fissures in human coronary thrombosis. J Atheroscler Res 1966; 6:1-17.
5. Brown B, Gallery C, Badger R, et al. Incomplete lysis of thrombus in the moderate underlying atherosclerotic lesion during intracoronary infusion of streptokinase for acute myocardial infarction: quantitative angiographic observations. Circulation 1986; 73:653-661.
6. Ambrose J, Tannenbaum M, Alexopoulos D, et al. Angiographic progression of coronary artery disease and the development of myocardial infarction. J. Am. Coll Cardiol 1988; 12:56-62.
7. Glagov S, Weisenberg E, Zarins C, et al. Compensatory enlargement of human atherosclerotic coronary arteries. N Engl J Med 1987; 316:1371-1375.
8. de Korte C, van der Steen A, Cepedes E, et al. Characterization of plaque components and vulnerability with intravascular ultrasound elastography. Phys Med Biol 2000; 45:1465-1475.
9. Cerqueira M. Current status of radionuclide tracer imaging of thrombi and atheroma. Semin Nucl Med 1999; 29:339-351.
10. Casscells W, Hathorn B, David M, et al. Thermal detection of cellular infiltrates in living atherosclerotic plaques: possible implications for plaque rupture and thrombosis. Lancet 1996; 347:1447-1451.

11. Moody A R, Allder S, Lennox G, et al. Direct magnetic resonance imaging of carotid artery thrombus in acute stroke. Lancet 1999; 353:122-123.
12. Hofman M B M, Wickline S A, Lorenz C H. Quantification of inplane motion of the coronary arteries during the cardiac cycle: Implications for acquisition window duration for MR flow quantification. Journal of Magnetic Resonance Imaging 1998, 8(3):568576.

Example 9

Preparing the Magnetic Particle

This example details a method for preparing a magnetic particle (shown in FIG. 7). In the current example, the vegetable oil matrix, suspended with iron oxide was 20% (v/v) and the surfactant was 2% (w/v). The suspended oil could be constituted with 1 to 4% (w/v) hydrophobically coated organo-soluble iron oxide (2% in present example). Hydrophobically coated iron oxide (iron oxide coating is achieved using fatty acids (e.g., oleic) or alternative hydrophobic constructs which when dissolved in organic solvent and pre-mixed with oil leads to the colloidal retention and suspension of the iron oxide. The solvent is removed, such as by rotary evaporation, and allowed to dry, such as under vacuum for 2-3 h at 50° C. In the present example, the 2% surfactant co-mixture included L-α-phosphatidylcholine, cholesterol, DPPE and phospholipid conjugated targeting ligand (e.g. biotinylated-DPPE and others) that were dissolved in chloroform (small amount of methanol may be added if required to achieve homogenous solution). The chloroform was evaporated off in vacuo at a maximum temperature of 45° C. using the rotary evaporator and allowed to remain overnight in a vacuum drying oven at 40° C.

The tube or flask containing the lipid film was probe sonicated (Branson Sonifier Ultrasonic Probe) for 2 min with ultra pure de-ionized water (0.2 mM filtered) until re-suspension of the lipids is complete. These contents were combined with the remaining aliquot of the water and glycerin in a 50 mL centrifuge tube and sonicated until a homogeneous colloidal solution is obtained. The contents were transferred to a Microfluidizer and homogenized at a pressure of 16,000 to 20,000 psi for 4 min using ice water in the cooling bath. After processing, the nanocolloid was transferred to a sterilized 30 mL serum vial, sealed under nitrogen and stored in the refrigerator.

The surface can be chemically cross-linked using a bislinker amine/acid by carbodiimide coupling protocol. The membrane of the particle can optionally be photo cross linked using beta carotene in the lipid film above by exposing it to UV irradiation at 254 nm, to enhance the stability as well as the integrity of the particle and for better retention of the iron oxide within the oil core.

The magnetic iron oxide core comprises a polycrystalline magnetic iron oxide core of magnetite or maghemite or the mixtures of both. Further metals can also be added to the magnetic iron core to increase magnetic strength. The core of the colloid that is contained in the polycrystalline magnetic iron oxide particles preferably has a size of 1-50 nm. The average particle sizes of the nanocolloid particles preferably have a size of 100-300 nm. Hydrophobic coating of the iron oxide particle could be any organo soluble coating. Surface and the lipid encapsulation of the each colloidal particle, can be tailor made with different homing ligands and drugs according to the need.

Table D below shows the stability of iron oxide particles before crosslinking (4-5 days) and after cross-linking (2 months).

TABLE D

| Inner core | Avg. particle size | | Zeta potential (Mv) | |
| --- | --- | --- | --- | --- |
| | Before cross-linking | After cross-linking | Before cross-linking | After cross-linking |
| 2% iron oxide loaded oil | 127 | 141 | −32.58 | −21.05 |
| 2% iron oxide loaded oil | 224 | 235 | −28.32 | −25.52 |

Example 10

Dynamic Light Scattering Measurement

Figure 8:
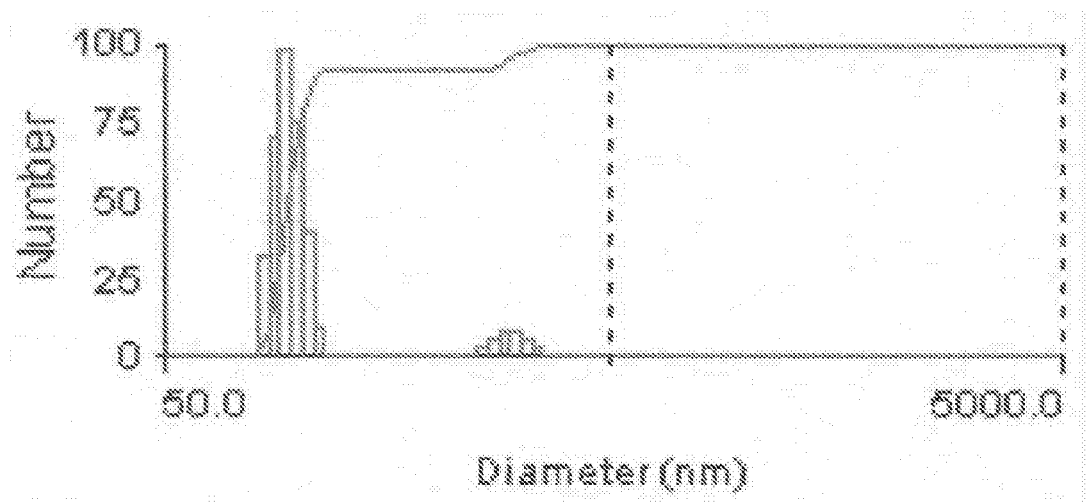
FIG. 8 depicts the hydrodynamic diameter of a lipid-encapsulated magnetic oxide particle.
Figure 9:
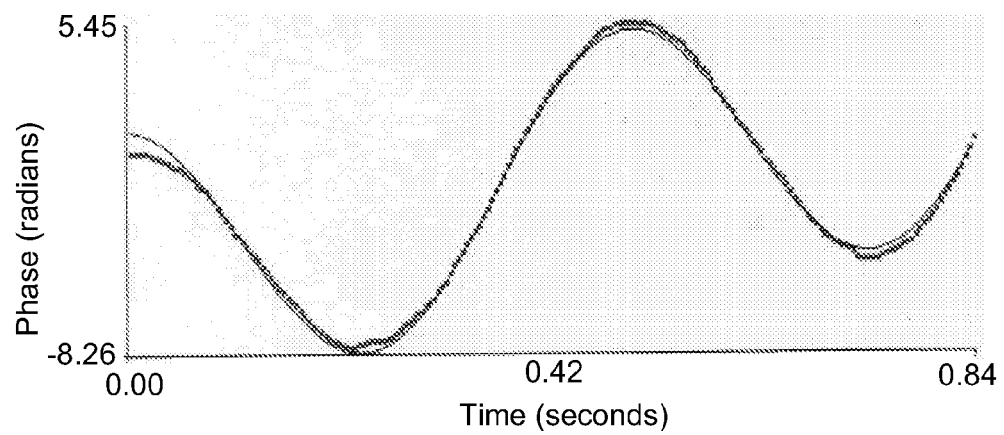
FIG. 9 depicts the zeta potential of a lipid-encapsulated magnetic oxide particle.

The hydrodynamic diameter of the colloidal aggregates and the zeta potential were calculated by dynamic and electrophoretic light scattering techniques using Brookhaven Instruments Corporation's Zeta Sizer-Zeta Potential Analyzer. The hydrodynamic diameter and zeta potential of the nano-colloid were in the range between 130-300 nm and −23 to −40 mV respectively (See FIGS. 8 and 9).

Example 11

Estimation of Iron Concentration

The concentration of iron is determined in the liquid samples by using inductively coupled plasma-mass spectroscopy. Iron concentrations are found to be anywhere between 1000-3500 mg/g.

Example 12

Transmission Electron Microscope

Figure 10:
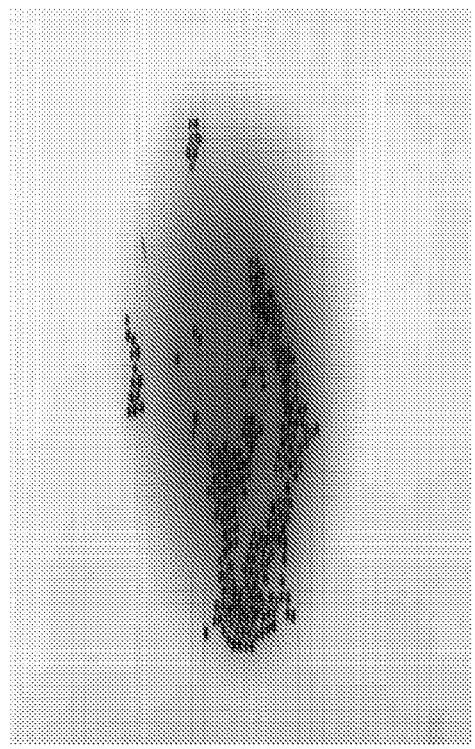
FIG. 10 shows transmission electron microscopy of the distribution of particle size and the size of aggregates in a suspension of a lipid-encapsulated magnetic oxide particle.

The distribution of particle size in the suspensions and the size of the aggregates were evaluated by transmission electron microscopy (FIG. 10). Transmission electron micrograph of the colloid particles reveal that the colloid particles were spherical in nature and the core of the each particle was constituted with multiple iron oxide particles. Average particle sizes of the colloid particles could be anywhere in the range between 10 nm to 2 micron, but are preferably 100 to 300 nm.

Example 13

Magnetic Measurement

Figure 11:
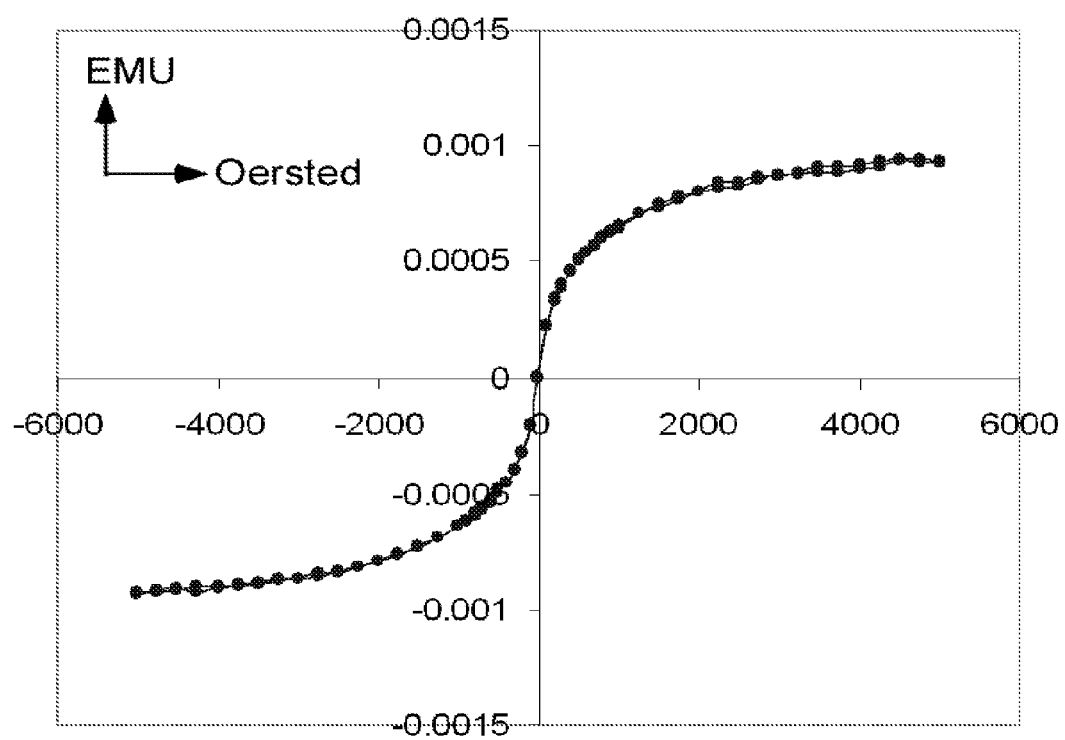
FIG. 11 shows measurements of the magnetic properties of a lipid-encapsulated magnetic oxide particle as measured using a Vibrating Sample Magnetometer. The negligible values of coercivity and remanent magnetization (ir/is 8 100%=0.36%) indicate that the nanoparticles show a superparamagnetic effect, which is required for in vivo application.
Figure 12:
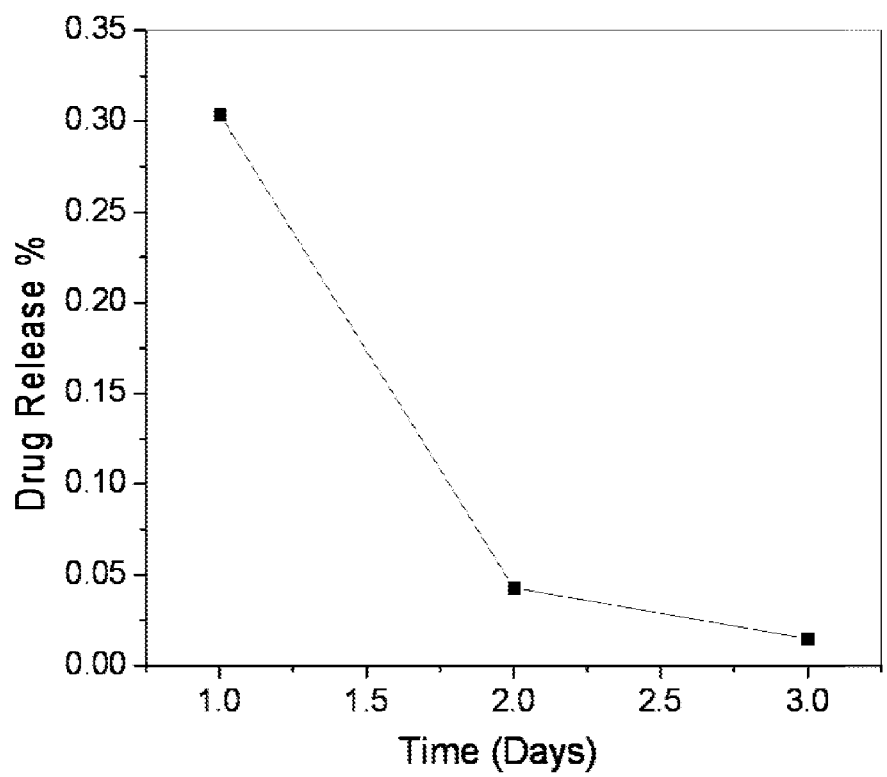
FIG. 12 shows the results of a dissolution study of a typical hydrophobic drug (fumagillin) from a lipid-encapsulated magnetic oxide particle. The kinetics of drug release indicates a loading efficiency of 98-99% on the surface of the particle or inside the core of the particle.

The measurements of magnetic properties of the emulsion were performed using Vibrating Sample Magnetometer (FIG. 11). The sample was placed inside the magnet with continuously varying uniform magnetic field given on X axis in Oersted. The vibrating magnetic sample induced a change in the magnetic flux. The change in the magnetic flux induced a voltage proportional to the magnetic moment of the sample given in emu on Y-axis. The saturation magnetic moment was 9.331E-4 emu, while the remanance (sample magnetic moment after the external magnetic field is 0) was 3.4E-6 emu. The strength of coercive external magnetic field required to reverse magnetic moment of the sample from saturation down to 0 was equal to 1.519 Oersted. The negligible values of coercivity and remanent magnetization (Ir/Is*100%=0.36%) indicate that the particles show a superparamagnetic effect, which is required for in vivo application.

Example 14

Kinetics of Drug Release Experiment

This example describes the results of a dissolution study of a typical hydrophobic drug, fumagillin. The results indicate that the loaded iron oxide nano-colloid released less than 1% of drug fumagillin after 3 days. This indicates a loading efficiency of 98-99% of drugs on the surface of the particle or inside the core of the particle. This experiment suggests that drug could be adequately retained in circulation until clearance or targeting has occurred. Slow diffusion or particle breakdown would release the drug locally. The constrained circulation, the anticipated decrease in dose given, and the targeting enhanced concentration of the particle at the pathology would all contribute to enhanced efficacy with reduced toxicity versus a systemically administered equally effective drug level. Moreover, the imaging combination would be useful to assess whether the drug has reached its destination in adequate therapeutic dose as well as to predict, based on the drug dose delivered, the anticipated magnitude of response.

Example 15

Magnetic Resonance Imaging

Figure 13:
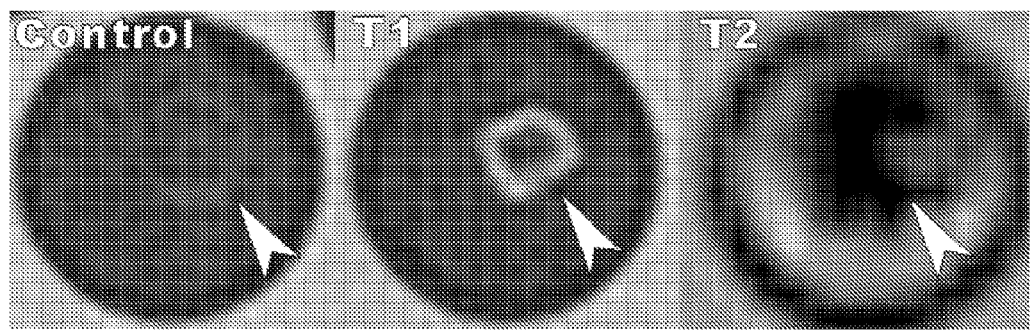
FIG. 13 shows magnetic resonance (MR) T1 and T2 properties of a lipid-encapsulated magnetic oxide particle that targets fibrin-rich clots (arrows). Untreated control clot is not well seen. Treated clots are detected on T1 and T2 weighted images.
Figure 14:
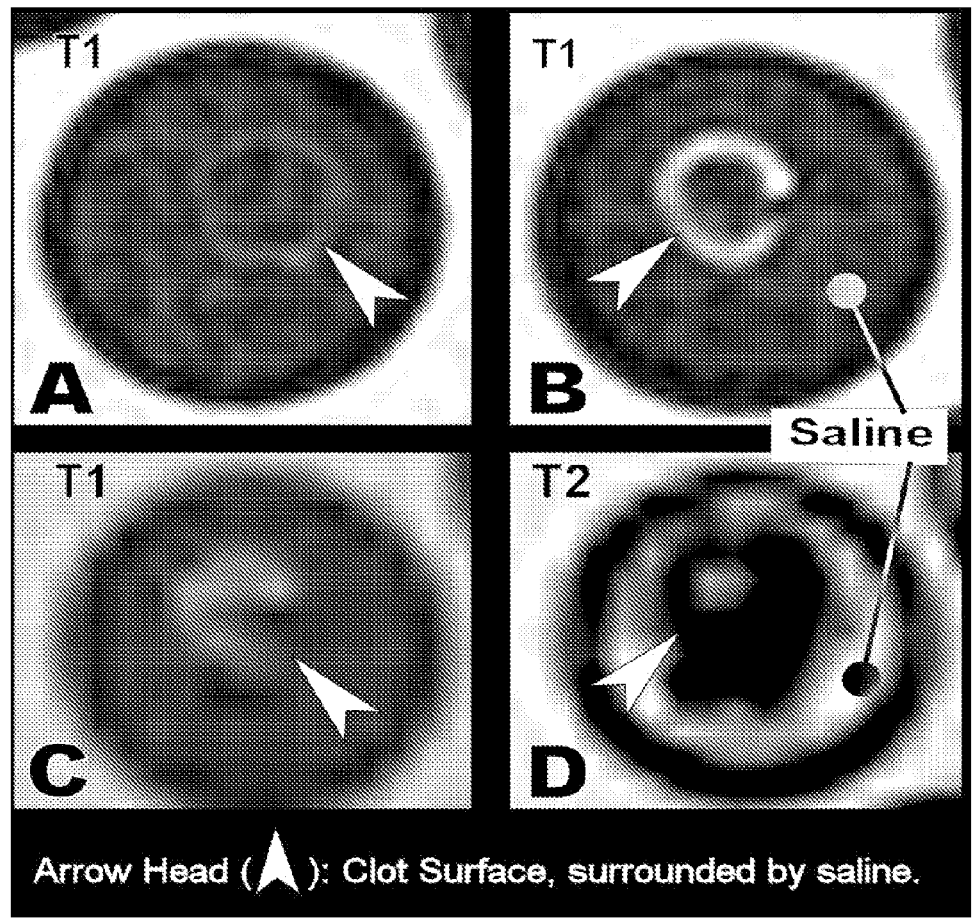
FIG. 14 shows magnetic resonance (MR) T1 and T2 properties of a lipid-encapsulated magnetic oxide particle that targets fibrin-rich clots. Targeted to fibrin clots, the agent produced signal enhancement on high resolution (0.3× 0.3×1.2 mm$^3$) T1-w TSE imaging (b) (SNR=26); whereas the control clot (a) that bound no agent, had an SNR=10, similar to surrounding saline. Lower resolution gradient echo imaging also shows enhancement on T1-w (c), but on T2-w images with longer TE (d) revealed characteristic signal dropout (blooming into many neighboring voxels) produced by the bound agent (but not on the control clot). (e) As demonstrated using in vitro atherosclerotic carotid artieries, these larger, fibrin-specific superparamagnetic particles provide highly sensitive, bright-contrast detection of microthrombi exposed in ruptured plaque.
Figure 14:
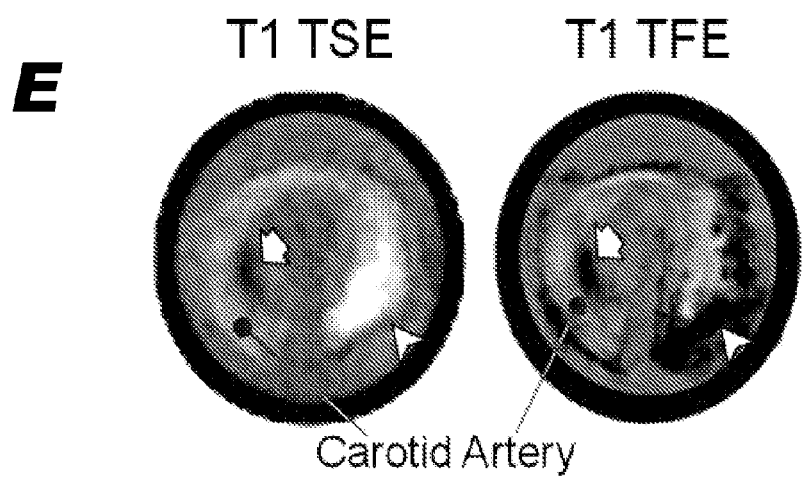
Figure 15:
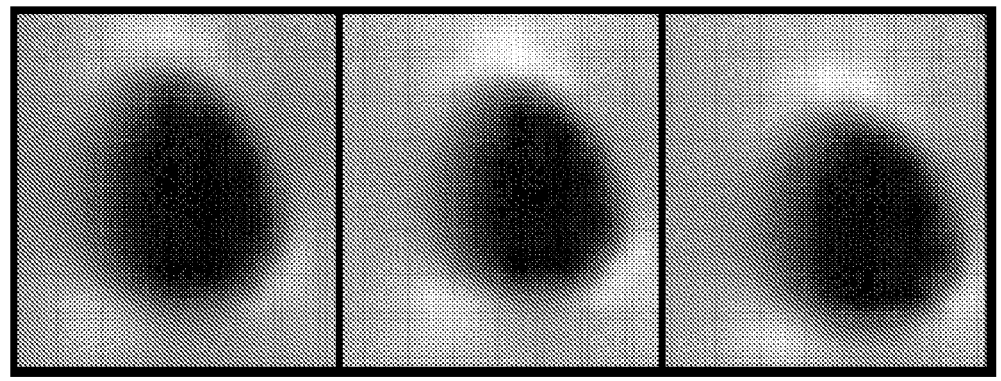
FIG. 15 depicts the results of a magnetic resonance imaging study with a particle of the invention. Multi-echo spin echo acquisition shows increasing T2 effects with increasing concentration and echo time (i.e. T2 weighting).
Figure 16:
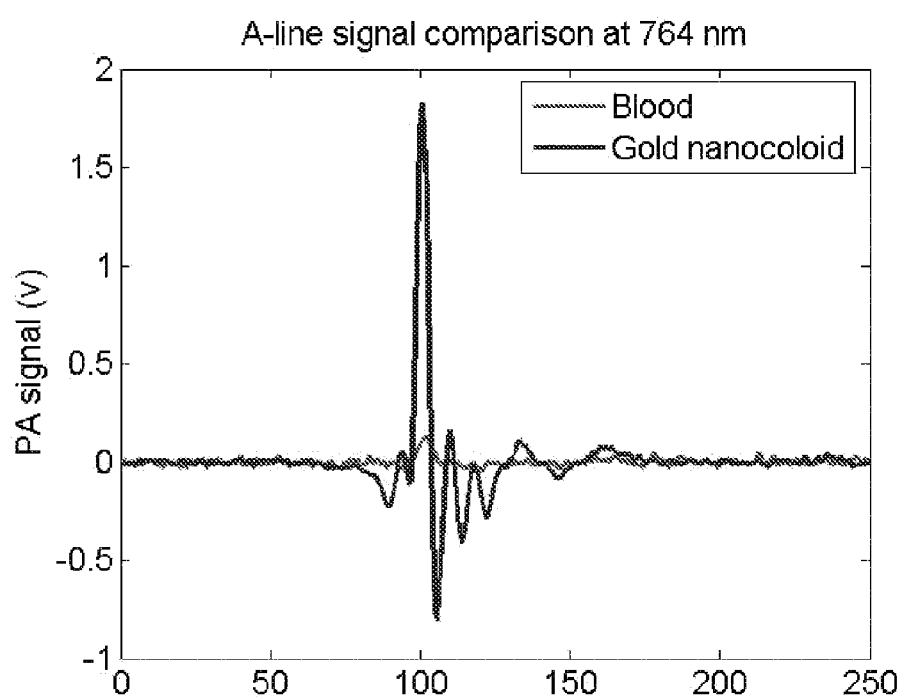
FIG. 16 depicts an A-line signal comparison of whole blood a photoacoustic tomographic signal of gold nanocolloid in suspension at 764 nm laser.

The MR T1 and T2 properties of the nanocolloid were determined using serial dilutions of the particle from 100% to 1% and MR acquisitions including Look-Locker (inversion recovery) and multi-echo gradient-echo techniques (See FIGS. 13 and 14). To assess signal on both T1- and T2-weighted images, functionalized particles were targeted to clot surfaces with biotin and an antibody targeted to fibrin-rich thrombi (n=7) suspended in saline in vitro; one clot served as an untreated control reference. Imaging of the clots was performed at 1.5 T using a high-resolution (0.3× 0.3×1.2 mm3) 3D T1-weighted turbo spin-echo sequence for ROI analysis and lower-resolution (1×1×5 mm3) gradient-echo imaging, both T1- and T2*-weighted, for visual inspection.

At higher concentrations in solution, the T2* effects dominated and produced dark distorted images typical to iron oxide particles. When bound to the outer surface of the fibrin-rich clots, the nano-colloid produced bright enhancement on T1-weighted imaging (SNR=26); whereas the control clot, which received no particle, was poorly discerned from surrounding saline (SNR=10). On T2-weighted images, characteristic "blooming" effects were produced by the bound particle, but not on the control. Using pharmacokinetic parameters and models for similar lipid-encapsulated emulsion particles, the systemic concentration of this nano-colloid particle for a typical in vivo application was projected to be less than the 1% dilution upon injection and approximately 0.03% of this concentration in 20 minutes, which suggest that, although the particles are constrained to the vasculature, the background levels will be negligible soon after injection leaving only the bound particle visible. Moreover, the dual T1 and T2 contrast features of this particle obviates the need for pre-contrast baseline images.

These data suggest that this novel nano-colloidal particle could have potential for detecting specific cell surface markers accessible from the circulation, such as fibrin and integrins, soon after systemic administration and targeting has occurred. Moreover, both the larger particle size and ability to image rapidly will preclude confounding the source of T1w contrast with extravascular macrophage phagocytosis, which is the situation with virtually all iron oxide based particles to date. The rapid reticuloendothelial clearance of the particles. In addition, fibrin-specific superparamagnetic nanocolloids may provide highly sensitive, bright-contrast detection of microthrombi exposed in ruptured plaque. The combination of high MR sensitivity and the imaging speed advantages of short T1-weighted pulse sequences may even overcome the cardiac motion barrier to MR coronary molecular imaging.

REFERENCES FOR EXAMPLES 9-15

1. Selective inductive heating of lymph nodes; 46Gilchrist, R. K., R. Medal, W. D. Shorey, R. C. Hanselman, J. C. Parrott, and C. B. Taylor. Ann. Surg. 146:596-606, 1957
2. Superparamagnetic Iron Oxide Nanoparticle Probes for Molecular Imaging; Thorek, Daniel; Chen, Antony; Czupryna, Julie; Tsourkas, Andrew1, Annals of Biomedical Engineering, Volume 34, Number 1, January 2006, pp. 23-38(16)
3. Encapsulated magnetite particles for biomedical application; Katharina Landfester and Liliana P Ram'irez, J. Phys.: Condens. Matter 15 (2003) S1345-S1361 PII: S0953-8984(03)54858-5
4. Contrast nanoparticles for MRI based on iron oxide nanoparticles prepared by laser pyrolysis; M. P. Moralesa, *, O. Bomati-Miguela, R. P!erez de Alejob, J. Ruiz-Cabellob, S. Veintemillas-Verdaguera, K. O'Grady; Journal of Magnetism and Magnetic Materials 266 (2003) 102-109
5. Preparation of poly-caprolactone nanoparticles containing magnetite for magnetic drug carrier; J. Yanga, 1, S.-B. Parkb, 2, Ho-Geun Yoonc, 3, Y.-M. Huhd, and S. Haam; International Journal of Pharmaceutics; Volume 324, Issue 2, 6 Nov. 2006, Pages 185-190
6. Encapsulation of nanosized magnetic iron oxide by polyacrylamide via inverse miniemulsion polymerization; Z. Z. Xu, C. C. Wang, W. L. Yang, Y. H. Deng and S. K. Fu Journal of Magnetism and Magnetic Materials; Volume 277, Issues 1-2, June 2004, Pages 136-143
7. Preparation and characterization of narrow sized (o/w) magnetic emulsion; F. Montagnea, O. Mondain-Monvalb, C. Pichota, H. Mozzanegac and A. Elaïssari; Journal of Magnetism and Magnetic Materials; Volume 250, September 2002, Pages 302-312
8. Preparation and characterization of biodegradable magnetic carriers by single emulsion-solvent evaporation; Xianqiao Liva, Michael D. Kaminskib, Judy S. Rifflec, Haitao Chena, Michael Tornoa, Martha R. Finckb, LaToyia Taylora and Axel J. Rosengart; Journal of Magnetism and Magnetic Materials; Volume 311, Issue 1, April 2007, Pages 84-87
9. Magnetic and conducting Fe3O4-cross-linked polyaniline nanoparticles with core-shell structure; Jianguo Dengb, a, Xiaobing Ding a, Wenchuan Zhanga, Yuxing Peng, a, Jianhua Wangb, Xingping Longb, Pei Lic and Albert S. C. Chan; Polymer; Volume 43, Issue 8, April 2002, Pages 2179-2184
10. Surface Modification and Characterization of Magnetic Polymer Nanospheres Prepared by Miniemulsion Polymerization; Xianqiao Liu, Yueping Guan, Zhiya Ma, and Huizhou Liu; Langmuir, 20 (23), 10278-10282, 2004. 10.1021/la0491908 S0743-7463(04)09190-5
11. Preparation of magnetic polymeric particles via inverse microemulsion polymerization process; Y. Denga, L. Wanga, W. Yanga, S. Fu, a and A Elaïssari; Journal of Magnetism and Magnetic Materials; Volume 257, Issue 1, February 2003, Pages 69-78
12. J. Bibette, J. Magn. Magn. Mater. 122 (1993) 37.
13. R. E. Rosenweig, Int. Sci. Technol. (1966) 48.
14. S. Papell, US Patent, 1965.
15. K. Raj, R. Moskowitz, J. Magn. Magn. Mater. 85 (1990) 233
16. S. W. Charles, J. Magn. Magn. Mater. 65 (1987) 350.
17. S. Roath, J. Magn. Magn. Mater. 122 (1993) 329.
18. J. Roger, J. N. Pons, R. Massart, Eur. Phys. J. 5 (1999) 321.
19. K. J. Davies, S. Wells, S. W. Charles, J. Magn. Magn. Mater. 122 (1993) 24.
20. N. Feltin, M. P. Pileni, Langmuir 13 (1997) 3927.
21. P. A. Dresco, V. S. Zaitsev, R. J. Gambino, B. Chu, Langmuir 15 (1999) 1945.

What is claimed is:

1. A particle comprising an outer layer formed over an inner core, wherein:
   a. the inner core is a solution, a mixture, or a suspension that comprises at least one metal atom in the form of an organometallic compound or organo-coated metal compound and a separate polysorbate, wherein the metal atom is selected from the group of metal atoms consisting of metals with an atomic number greater than seventeen and less than eighty-four; and
   b. the outer layer comprises an amphiphillic material.

2. The particle of claim 1, wherein the metal atom is selected from the group consisting of manganese, copper, bismuth, ytterbium and gold.

3. The particle of claim 1, wherein the outer layer further comprises at least one metal atom.

4. The particle of claim 1, wherein the particle comprises at least 100,000 metal atoms.

5. The particle of claim 1, wherein the metal is selected from the group consisting of metals that have a K-edge in the x-ray energy band of CT, metals that have paramagnetic or superparamagnetic properties, metals that have optical, near-infrared, or photoacoustic properties, metals that have sound scattering properties, and metals that have a radioactive particle emission.

6. The particle of claim 1, wherein the metal atom comprises a metal compound selected from the group consisting of a metal oxide, metal sulphide, metal phosphate, metal carbonate, metal chromate, mixed metal oxide, metal spinels, and a combination thereof.

7. The particle of claim 6, wherein the metal oxide is selected from the group consisting of magnetite, maghemite, and a combination thereof.

8. The particle of claim 6, wherein the metal oxide has the formula $MFe_2O_4$, where M is selected from the group consisting of Fe, Mn, Co, Ni, Mg, Au, Cu, Zn, Ba, Sr, Pt, Tl, Ti, and a combination thereof.

9. The particle of claim 6, wherein the mixed metal oxide or spinels is selected from the group consisting of gold oxide, nickel oxide, magnesium oxide, manganese oxide, and cobalt oxide.

10. The particle of claim 1, wherein the outer layer further comprises one or more molecules selected from the group consisting of a surfactant, a bioactive agent, a targeting agent, and an imaging agent.

11. The particle of claim 10, wherein the outer layer is comprised of an amphiphilic material selected from the group consisting of natural materials, synthetic materials, semisynthetic materials, and a combination thereof.

12. The particle of claim 10, wherein the imaging agent is selected from the group of agents detectable by optical imaging, near-infrared imaging, NMR imaging, MRI imaging, x-ray imaging, CT imaging, K-edge imaging, ultrasound imaging, photoacoustic imaging, acoustic optical imaging, microwave imaging, nuclear imaging and combinations thereof.

13. The particle of claim 1, wherein the organo-coated metal compound of the inner core comprises at least one structure selected from the group consisting of an inverted micelle, a hydrophobically-coated metal particle, and combinations thereof.

14. The particle of claim 13, wherein the inverted micelle comprises an amphiphilic polymer and metal.

15. The particle of claim 1, wherein the organometallic compound is selected from the group consisting of metal polysorbate compounds, metal surfactant compounds, metal aliphatic compounds and metal aromatic hydrophobic compounds and combinations thereof.

16. The particle of claim 13, wherein the hydrophobically-coated metal particle is selected from the group consisting of metal surfactant compounds, metal natural polymer compounds, metal synthetic polymer compounds, metal aliphatic compounds, metal aromatic hydrophobic compounds and combinations thereof.

17. The particle of claim 13, wherein the inner core is comprised of a plurality of inverted micelles.

18. The particle of claim 17, wherein the plurality of inverted micelles comprise substantially all the metal atoms comprising the particle.

19. The particle of claim 16, wherein the metal aliphatic compounds are metal fatty acid compounds.

20. The particle of claim 16, wherein the metal aliphatic compounds are derived from oleic acid.

21. The particle of claim 20, wherein the metal aliphatic compound is selected from the group consisting of manganese oleate, copper oleate, bismuth oleate, and yterrbium oleate.

* * * * *

UNITED STATES PATENT AND TRADEMARK OFFICE
CERTIFICATE OF CORRECTION

PATENT NO. : 9,446,150 B2  
APPLICATION NO. : 12/682094  
DATED : September 20, 2016  
INVENTOR(S) : Gregory M. Lanza et al.

Page 1 of 1

It is certified that error appears in the above-identified patent and that said Letters Patent is hereby corrected as shown below:

In the Specification

Column 1, Lines 14–18 delete:
"The present invention was made, at least in part, with support by the National Institutes of Health Siteman Center of Cancer Nanotechnology Excellence grant number U54 CA119342. Accordingly, the United States Government may have certain rights in the invention"
And replace with:
-- This invention was made with government support under HL073646, NS059302 and CA119342 awarded by the National Institutes of Health. The government has certain rights in the invention --.

Signed and Sealed this  
Fifth Day of May, 2020

Andrei Iancu  
*Director of the United States Patent and Trademark Office*